US009520565B2

(12) United States Patent
Wang et al.

(10) Patent No.: US 9,520,565 B2
(45) Date of Patent: Dec. 13, 2016

(54) INDACENO DERIVATIVES AS ORGANIC SEMICONDUCTORS

(75) Inventors: Changsheng Wang, Durham (GB); Nicolas Blouin, Southampton (GB); Mansoor D'Lavari, Bude (GB); Steven Tierney, Southampton (GB); Lana Nanson, Southampton (GB)

(73) Assignee: MERCK PATENT GMBH, Darmstadt (DE)

( * ) Notice: Subject to any disclaimer, the term of this patent is extended or adjusted under 35 U.S.C. 154(b) by 175 days.

(21) Appl. No.: 14/129,577

(22) PCT Filed: May 30, 2012

(86) PCT No.: PCT/EP2012/002290
§ 371 (c)(1),
(2), (4) Date: Dec. 27, 2013

(87) PCT Pub. No.: WO2013/000532
PCT Pub. Date: Jan. 3, 2013

(65) Prior Publication Data
US 2014/0131627 A1 May 15, 2014

(30) Foreign Application Priority Data
Jun. 28, 2011 (EP) .................................... 11005251

(51) Int. Cl.
*H01B 1/12* (2006.01)
*H01L 51/00* (2006.01)
*C07D 513/04* (2006.01)

(52) U.S. Cl.
CPC ......... *H01L 51/0036* (2013.01); *C07D 513/04* (2013.01); *H01L 51/0074* (2013.01)

(58) Field of Classification Search
CPC .... H01L 51/0036; H01L 51/0074; H01B 1/12; C08G 61/12; C07D 513/04; C07C 13/62
USPC .......... 252/511, 500; 549/41, 3, 50; 528/380
See application file for complete search history.

(56) References Cited

U.S. PATENT DOCUMENTS

| 7,714,098 B2 | 5/2010 | Merck | |
|---|---|---|---|
| 8,288,013 B2 | 10/2012 | Morishita | |
| 8,299,247 B2 | 10/2012 | Morishita | |
| 8,481,177 B2 | 7/2013 | Morishita | |
| 2002/0132134 A1 | 9/2002 | Hu et al. | |
| 2009/0036643 A1 | 2/2009 | Marks et al. | |
| 2009/0314997 A1* | 12/2009 | Heeney ................. | C07D 495/04 252/500 |
| 2010/0019659 A1 | 1/2010 | Morishita | |
| 2011/0226999 A1 | 9/2011 | Tierney et al. | |
| 2011/0275814 A1 | 11/2011 | Morishita | |
| 2012/0153274 A1 | 6/2012 | Sonar et al. | |
| 2012/0161117 A1 | 6/2012 | Chen et al. | |
| 2012/0306362 A1 | 12/2012 | Morishita | |
| 2013/0256604 A1* | 10/2013 | Blouin ................. | C07D 495/04 252/500 |
| 2014/0158949 A1 | 6/2014 | Wang et al. | |
| 2014/0252279 A1* | 9/2014 | Wang ................. | H01L 51/0043 252/511 |
| 2015/0076418 A1* | 3/2015 | Blouin ................ | C08K 3/04 252/511 |
| 2015/0144847 A1* | 5/2015 | D'Lavari ............. | C08G 61/126 252/511 |

FOREIGN PATENT DOCUMENTS

| CN | 101798310 A | 8/2010 | |
|---|---|---|---|
| EP | 2045848 A1 | 4/2009 | |
| JP | 2004335610 A | 11/2004 | |
| JP | 2008504379 A | 2/2008 | |
| WO | 2009011327 A1 | 1/2009 | |
| WO | 2009/017798 A1 | 2/2009 | |
| WO | 2010/020329 A1 | 2/2010 | |
| WO | 2011/025454 A1 | 3/2011 | |
| WO | WO2013028441 A2 * | 2/2013 | ............. C08G 61/12 |

OTHER PUBLICATIONS

English Translation of CN 201010118172, Aug. 11, 2010.*
International Search Report dated Jul. 25, 2012 issued in corresponding PCT/EP2012/002290 application (pp. 1-4).
G. Hughes et al., "New Pyrimidine—and Fluorene-Containing Oligo(arylene)s: Synthesis, Crystal Structures, Optoelectronic Properties and a Theoretical Study", Org. Biomol. Chem., vol. 1 (2003) pp. 3069-3077.
H. Usta et al., "Air-Stable, Solution-Processable n-Channel and Ambipolar Semiconductors for Thin-Film Transistors Based on the Indenofluorenebis(dicyanovinylene) Core", Journal of the American Chemical Society, vol. 130, No. 27 (2008) pp. 8580-8581.
H. Usta et al., "Design, Synthesis, and Characterization of Ladder-Type Molecules and Polymers. Air Stable, Solution-Processable n-Channel and Ambipolar Semiconductors for Thin-Film Transistors via Experiment and Theory", Journal of the American Chemical Society, vol. 131, No. 15 (2009) pp. 5586-5608.
H. Tian et al., "A Feasibly Synthesized Ladder-Type Conjugated Molecule as the Novel High Mobility n-Type Organic Semiconductor", Journal of Materials Chemistry, vol. 20 (2010) pp. 7998-8004.
W. Zhang et al., "Indacenodithiophene Semiconducting Polymers for High-Performance, Air-Stable Transistors", Journal of the American Chemical Society, vol. 132 (2010) pp. 11437-11439.
Y.C. Chang et al., "On the Air Stability of n-Channel Organic Field-Effect Transistors: A Theoretical Study of Adiabatic Electron Affinities of Organic Semiconductors", Journal of Physical Chemistry, vol. 114, No. 26 (2010) pp. 11595-11601.

(Continued)

*Primary Examiner* — Douglas Mc Ginty
(74) *Attorney, Agent, or Firm* — Millen, White, Zelano and Branigan, P.C.

(57) ABSTRACT

The invention relates to novel organic semiconducting compounds containing one or more dialkylidene-s-indacenodiheteroarene groups, methods for their preparation and educts or intermediates used therein, polymers, blends, mixtures and formulations containing them, the use of the compounds, polymers, blends, mixtures and formulations as semiconductor in organic electronic (OE) devices, especially in organic photovoltaic (OPV) devices, and to OE and OPV devices comprising these compounds, polymers, blends, mixtures or formulations.

28 Claims, No Drawings

(56) References Cited

OTHER PUBLICATIONS

JP 2014-517488 Office Action issued Mar. 10, 2016.
English translation of CN101798310 published Aug. 11, 2010 to Changchun Applied Chemistry.
English Translation of JP2004335610A published Nov. 25, 2004 to Saito Kazuhiro at NAT INST OF ADV IND & TECHNOL.

* cited by examiner

INDACENO DERIVATIVES AS ORGANIC SEMICONDUCTORS

FIELD OF THE INVENTION

The invention relates to novel organic semiconducting compounds containing one or more dialkylidene-s-indacenodiheteroarene groups, methods for their preparation and educts or intermediates used therein, polymers, blends, mixtures and formulations containing them, the use of the compounds, polymers, blends, mixtures and formulations as semiconductors in organic electronic (OE) devices, especially in organic photovoltaic (OPV) devices, and to OE and OPV devices comprising these compounds, polymers, blends, mixtures or formulations.

BACKGROUND OF THE INVENTION

Organic semiconducting (OSC) materials are receiving growing interest mostly due to their rapid development in the recent years and the lucrative commercial prospects of organic electronics.

One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies above 8%.

In order to obtain ideal solution-processible OSC molecules two basic features are essential, firstly a rigid π-conjugated core or backbone, and secondly suitable functionality of the aromatic cores in the OSC backbone. The former extends π-π overlaps, defines the primary energy levels of the highest occupied and lowest unoccupied molecular orbitals (HOMO and LUMO), enables both charge injection and transport, and facilitates optical absorption. The latter further fine-tunes the energy levers and enables solubility and hence processability of the materials as well as π-π interactions of the molecular backbones in the solid state.

A high degree of planarity reduces the energetic disorder of OSC backbones and accordingly enhances charge carrier mobilities. In prior art most of the polymeric OSCs with high charge carries mobilities are generally composed of fused ring aromatic systems, and are semicrystalline in their solid states. Such polymers are for example indacenodithiophene-benzothiadiazole copolymers, for which it was reported by Zhang et al., *J. Am. Chem. Soc.*, 2010, 132(33), 11437 that a hole mobility of 1 cm$^2$/V s was achieved.

Nevertheless, the structures of solubilising groups (e.g., the length, the regio-regularity, the spacial orientation of the alkyl chains etc.), have direct effects on the solubility and hence the processability of the OSC, on the planarity of the polymer backbone, on the inter-chain π-π interactions and on the HOMO-LUMO levels/bandgaps. For many applications, like e.g. OPV devices, optimisation of the electronic properties of the conjugated backbones by fine-tuning the solubilising functional groups can result in dramatic effects on the efficiencies.

The conventional method of introducing solubilising groups into cyclopentadiarene units like indacenodithiophene (Zhang et al., *J. Am. Chem. Soc.*, 2010, 132(33), 11437), is to alkylate the sp$^3$ carbon atoms of the cyclopentadienes contained in these fused ring structures. Due to the tetrahedral configuration of this carbon, the substituents have to take the orientation within a plane that is normal to the aromatic plane of the conjugated backbone, as shown by X-ray single crystal analysis by Hughes et al., *Org. Biomol. Chem.*, 2003, 1, 3069. These out-of-plane alkyl chains increase the inter-planar separation of the π-π backbones, reducing the degree of inter-molecular π-π interactions. However, from a synthetic point of view, multiple alkylation like for example tetraalkylation of the indacenodithiophene leads to difficulties of purication of the expected products due to the very similar polarities of the product and the incompletely alkylated impurities.

Thus there is still a need for organic semiconducting (OSC) materials that are easy to synthesize, especially by methods suitable for mass production, show good structural organization and film-forming properties, exhibit good electronic properties, especially a high charge carrier mobility, good processibility, especially a high solubility in organic solvents, and high stability in air. Especially for use in OPV cells, there is a need for OSC materials having a low bandgap, which enable improved light harvesting by the photoactive layer and can lead to higher cell efficiencies, compared to the polymers from prior art.

It was an aim of the present invention to provide compounds for use as organic semiconducting materials that do not have the drawbacks of prior art materials as described above, are easy to synthesize, especially by methods suitable for mass production, and do especially show good processibility, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that one or more of the above aims can be achieved by providing compounds, including small molecules, oligomers and conjugated polymers, containing one or more 4,9-dialkylidene-s-indacenodiheteroarene-2,7-diyl repeating units having the following structure

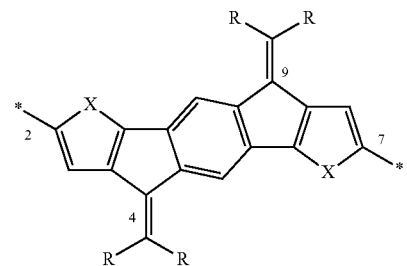

wherein R is e.g. alkyl or fluoroalkyl groups and X is e.g. S or Se.

The dialkylidene-s-indacenodiheteroarene as claimed in the present invention are solubilised using alkylidene groups R, of which the carbon atoms connecting to the ring systems are sp$^2$-hybridized instead of sp$^3$-hybridized. The sp$^2$-carbons permit the solubilising alkyl chains to adopt a coplanar conformation relative to the core/polymer backbone, thus facilitating cofacial aggregation in the solid state. This kind of coplanar orientation of the alkyls has been demonstrated by the crystal structures of polymers as disclosed in the examples of the present invention.

It was found that compounds comprising dialkylidene-s-indacenodiheteroarene units are attractive candidates for photovoltaic applications, specifically in bulk heterojunction (BHJ) photovoltaic devices. By the incorporation of the electron-donating dialkylidene-s-indacenodiheteroarene unit and an electron-accepting unit into a co-polymer i.e. a "donor-acceptor" polymer, a reduction of the bandgap can be achieved, which enables improved light harvesting properties in bulk heterojunction (BHJ) photovoltaic devices. Also, by varying the substituents at the alkylidene group the solubility and electronic properties of the compounds can be further optimised.

In prior art it has so far not been suggested using alkylidene and arylidene groups to solubilise indacenodiarene units. Usta et al., *J. Am. Chem. Soc.*, 2008, 130(7), 8580; Tian et al., *J. Mater. Chem.*, 2010, 20(37), 7998 and CN 101798310 A disclose monomeric dicyano substituted derivatives, and WO 2011/025454 A1 discloses polymeric dialkoxycarbonyl substituted derivatives, of indacenodithiophene or indacenofluorene.

However, there are significant differences between the compounds of the present invention and the compounds disclosed in prior art. Firstly, the alkylidene groups in the compounds of the present invention function as solubilising groups and the corresponding substituted indacenodiarenes remain π-electron donating units, whereas in the compounds of prior art, the electron-withdrawing cyano or alkoxycarbonyl substituents yield indacenodiarenes that behave as π-electron accepting units. Secondly, the current invention provides synthesis methods using aldehydes and ketones to incorporate the alkylidenes groups onto the target substrates under alkaline conditions, whereas the prior art discloses methods using the quinoid forms of indacenodiarenes reacting with either malononitrile or malonic esters under acidic conditions, which generally give poor yields with limited choice of structural variations.

SUMMARY OF THE INVENTION

The invention relates to compounds comprising one or more divalent units of formula I

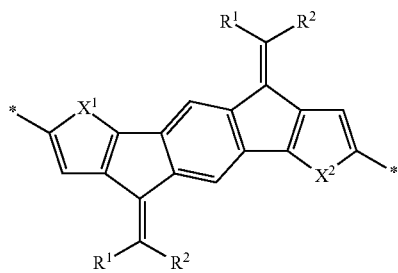

wherein
$X^1$ and $X^2$ are independently of each other O, S, Se, Te or CH=CH,
$R^1$ and $R^2$ independently of each other, and on each occurrence identically or differently, denote H, straight-chain, branched or cyclic alkyl, with 1 to 30 C atoms, in which one or more non-adjacent C atoms are optionally replaced by —O—, —S—, —NR$^0$—, —SiR$^0$R$^{00}$—, —CY$^1$=CY$^2$— or —C≡C— in such a manner that O and/or S atoms are not linked directly to one another, and in which one or more H atoms are optionally replaced by F, Cl, Br, I or CN, or $R^1$ and $R^2$, independently of each other, and on each occurrence identically or differently, denote aryl, heteroaryl, aryloxy or heteroaryloxy with 4 to 20 ring atoms which is optionally substituted, or $R^1$ and $R^2$ together form an alicyclic group with 1 to 20 C atoms, which is optionally fluorinated or alkylated,
$Y^1$ and $Y^2$ are independently of each other H, F, Cl or CN,
$R^0$ and $R^{00}$ are independently of each other H or optionally substituted $C_{1-40}$ carbyl or hydrocarbyl, and preferably denote H or alkyl with 1 to 12 C-atoms.

The invention further relates to a formulation comprising one or more compounds comprising a unit of formula I and one or more solvents, preferably selected from organic solvents.

The invention further relates to an organic semiconducting formulation comprising one or more compounds comprising a unit of formula I, one or more organic binders, or precursors thereof, preferably having a permittivity ∈ at 1,000 Hz and 20° C. of 3.3 or less, and optionally one or more solvents.

The invention further relates to the use of units of formula I as electron donor units in semiconducting polymers.

The invention further relates to a conjugated polymer comprising one or more repeating units, wherein said repeating units contain a unit of formula I and/or one or more groups selected from aryl and heteroaryl groups that are optionally substituted, and wherein at least one repeating unit in the polymer contains at least one unit of formula I.

The invention further relates to monomers containing a unit of formula I and further containing one or more reactive groups which can be reacted to form a conjugated polymer as described above and below.

The invention further relates to a semiconducting polymer comprising one or more units of formula I as electron donor units, and preferably further comprising one or more units having electron acceptor properties.

The invention further relates to the use of the compounds according to the present invention as electron donor or p-type semiconductor.

The invention further relates to the use of the compounds according to the present invention as electron donor component in semiconducting materials, formulations, blends, devices or components of devices.

The invention further relates to a semiconducting material, formulation, blend, device or component of a device comprising a compound according to the present invention as electron donor component, and preferably further comprising one or more compounds or polymers having electron acceptor properties.

The invention further relates to a mixture or blend comprising one or more compounds according to the present invention and one or more additional compounds which are preferably selected from compounds having one or more of semiconducting, charge transport, hole or electron transport, hole or electron blocking, electrically conducting, photoconducting or light emitting properties.

The invention further relates to a mixture or blend as described above and below, which comprises one or more compounds of the present invention and one or more n-type organic semiconductor compounds, preferably selected from fullerenes or substituted fullerenes.

The invention further relates to a formulation comprising one or more compounds, formulations, mixtures or blends according to the present invention and optionally one or more solvents, preferably selected from organic solvents.

The invention further relates to the use of compounds, formulations, mixtures and blends of the present invention as charge transport, semiconducting, electrically conducting, photoconducting or light emitting material in optical, electrooptical, electronic, electroluminescent or photoluminescent devices, or in components of such devices, or in assemblies comprising such devices or components The invention further relates to a charge transport, semiconducting, electrically conducting, photoconducting or light emitting material or component comprising one or more compounds, formulations, mixtures or blends of the present invention.

The invention further relates to an optical, electrooptical, electronic, electroluminescent or photoluminescent component or device, or a component thereof, or an assembly comprising it, which comprises one or more compounds, formulations, mixtures, blends or components of the present invention.

The optical, electrooptical, electronic, electroluminescent and photoluminescent devices include, without limitation, organic field effect transistors (OFET), organic thin film transistors (OTFT), organic light emitting diodes (OLED), organic light emitting transistors (OLET), organic photovoltaic devices (OPV), organic solar cells, laser diodes, Schottky diodes, photoconductors and photodetectors.

The components of the above devices include, without limitation, charge injection layers, charge transport layers, interlayers, planarising layers, antistatic films, polymer electrolyte membranes (PEM), conducting substrates and conducting patterns.

The assemblies comprising such devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

In addition the compounds, formulations, mixtures or blends of the present invention can be used as electrode materials in batteries and in components or devices for detecting and discriminating DNA sequences.

DETAILED DESCRIPTION OF THE INVENTION

The compounds, monomers and polymers of the present invention are easy to synthesize and exhibit advantageous properties. The conjugated polymers of the present invention show good processability for the device manufacture process, high solubility in organic solvents, and are especially suitable for large scale production using solution processing methods. At the same time, the co-polymers drived from monomers of the present invention and electron accepting monomers show low bandgaps, high charge carrier mobilities, high external quantum efficiencies in BHJ solar cells, good morphology when used in p/n-type blends e.g. with fullerenes, high oxidative stability, and a long lifetime in electronic devices, and are promising materials for organic electronic OE devices, especially for OPV devices with high power conversion efficiency.

The unit of formula I is especially suitable as (electron) donor unit in p-type semiconducting compounds, polymers or copolymers, in particular copolymers containing both donor and acceptor units, and for the preparation of blends of p-type and n-type semiconductors which are useful for application in bulk heterojunction photovoltaic devices.

In addition, the compounds show the following advantageous properties:

i) Indacenodiarenes which include s-indacenodifuran, s-indacenoselenophene, s-indacenotellurophene and indenofluorene can be solubilised by the method of the current invention through Knoevenagel condensation with a variety of carbonyl compounds in good to high yields. This method is superior to the conventional tetraalkylation of these compounds as disclosed in prior art (see Zhang et al., *J. Am. Chem. Soc.,* 2010, 132(33), 11437) in both yield and ease of purification.

ii) Dialkylidene indacenodiarenes can be easily functionalised at specific positions through e.g., halogenation with N-halosuccinimide, elemental halogen, or through lithiation with alkyllithium and lithium amides then react with a halogenations reagent, alkyl borates, trialkylstannyl chlorides or zink chloride. These functionalise indacenodiarenes can be used to prepare a wide range of new semiconducting molecular materials as well as new homopolymers and copolymers through transition metal catalysed coupling methods such as Yamamoto coupling, Suzuki coupling or Stille coupling.

iii) Dialkylidene indacenodiarenes-based molecules and polymers are expected to possess a higher degree of planarity compared with the tetraalkyl analogues. In the latter case, the solubilising alkyl groups sitting on the two $sp^3$ carbon atoms take a tetrahedral configuration and have to stay out of the π-molecular planes. This tetrahedral configuration will doubtlessly hinder the π-π interactions of the conjugated molecular backbone and increase the energetic disorder of the OSCs. The indacenodiarenes in this invention, however, are solubilised using dialkylidene groups, of which the carbon atoms connecting to the ring systems are $sp^2$ carbons instead and become more planar. In this context, materials using dialkylidene indacenodiarenes as building blocks/monomers are expected to exhibit higher charge carrier mobilities compared to the corresponding tetraalkyl analogues.

iv) Similar to the know tetraalkyl-s-indacenodithiophenes, dialkylidene indacenodiarenes are also π-donor units. When polymerized with π-electron accepting monomers, low bandgap conjugated polymers are synthesized. Analogously, when these π-donor units are mono-/di-capped with π-acceptors or π-electron acceptors are mono-/di-capped with these π-electron donating indacenodiarene units, low bandgap molecular materials are to be synthesized. Both the polymeric and molecular low bandgap materials are potential donor candidates for use in organic photovoltaic solar cells.

v) By fine-tuning the LUMO levels of then-electron accepting units, the donor-acceptor materials synthesized using dialkylidene indacenodiarenes and suitable acceptors units can exhibit ambipolar charge transport behaviour in field-effect transistors.

The synthesis of the unit of formula I, its functional derivatives, compounds, homopolymers, and co-polymers can be achieved based on methods that are known to the skilled person and described in the literature, as will be further illustrated herein.

Above and below, the term "polymer" generally means a molecule of high relative molecular mass, the structure of which essentially comprises the multiple repetition of units derived, actually or conceptually, from molecules of low relative molecular mass (*Pure Appl. Chem.,* 1996, 68, 2291). The term "oligomer" generally means a molecule of intermediate relative molecular mass, the structure of which essentially comprises a small plurality of units derived, actually or conceptually, from molecules of lower relative molecular mass (*Pure Appl. Chem.,* 1996, 68, 2291). In a preferred sense according to the present invention a polymer means a compound having >1, i.e. at least 2 repeating units, preferably 5 repeating units, and an oligomer means a compound with >1 and <10, preferably <5, repeating units.

Above and below, in a formula showing a unit or a polymer, like formula I and its subformulae, an asterisk ("*") denotes a linkage to an adjacent unit or group, and in case of a polymer a link to an adjacent repeating unit or to a terminal group in the polymer chain.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291).

The term "small molecule" means a monomeric compound which typically does not contain a reactive group by which it can be reacted to form a polymer, and which is designated to be used in monomeric form. In contrast thereto, the term "monomer" unless stated otherwise means a monomeric compound that carries one or more reactive functional groups by which it can be reacted to form a polymer.

The terms "donor"/"donating" and "acceptor"/"accepting", unless stated otherwise, mean an electron donor or electron acceptor, respectively. "Electron donor" means a chemical entity that donates electrons to another compound or another group of atoms of a compound. "Electron acceptor" means a chemical entity that accepts electrons transferred to it from another compound or another group of atoms of a compound. (see also U.S. Environmental Protection Agency, 2009, Glossary of technical terms, http://www.epa.gov/oust/cat/TUMGLOSS.HTM).

The term "leaving group" means an atom or group (charged or uncharged) that becomes detached from an atom in what is considered to be the residual or main part of the molecule taking part in a specified reaction (see also *Pure Appl. Chem.*, 1994, 66, 1134).

The term "conjugated" means a compound containing mainly C atoms with $sp^2$-hybridisation (or optionally also sp-hybridisation), which may also be replaced by hetero atoms. In the simplest case this is for example a compound with alternating C—C single and double (or triple) bonds, but does also include compounds with units like 1,4-phenylene. "Mainly" means in this connection that a compound with naturally (spontaneously) occurring defects, which may lead to interruption of the conjugation, is still regarded as a conjugated compound.

Unless stated otherwise, the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1, 2, 4-trichlorobenzene. Unless stated otherwise, 1,2,4-trichlorobenzene is used as solvent. The degree of polymerization, also referred to as total number of repeating units, n, means the number average degree of polymerization given as $n=M_n/M_U$, wherein $M_n$ is the number average molecular weight and $M_U$ is the molecular weight of the single repeating unit, see J. M. G. Cowie, *Polymers: Chemistry & Physics of Modern Materials*, Blackie, Glasgow, 1991.

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

The term "hetero atom" means an atom in an organic compound that is not a H- or C-atom, and preferably means N, O, S, P, Si, Se, As, Te or Ge.

A carbyl or hydrocarbyl group comprising a chain of 3 or more C atoms may be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi- or tricyclic aromatic or heteroaromatic group with 4 to 30 ring C atoms that may also comprise condensed rings and is optionally substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, P-Sp-, optionally substituted silyl, or carbyl or hydrocarbyl with 1 to 40 C atoms that is optionally substituted and optionally comprises one or more hetero atoms, and is preferably alkyl, alkoxy, thiaalkyl, alkylcarbonyl, alkoxycarbonyl or alkoxycarbonyloxy with 1 to 20 C atoms that is optionally fluorinated, and R$^0$, R$^{00}$, X$^0$, P and Sp have the meanings given above and below.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thieno-thiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene preferably 2-thiophene, selenophene, preferably 2-selenophene, thieno[3,2-b]thiophene, indole, isoindole, benzofuran, benzothiophene, benzodithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, all of which can be unsubstituted, mono- or polysubstituted with L as defined above. Further examples of heteroaryl groups are those selected from the following formulae An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl) ethyl, 3-(methoxycarbonyl)propyl, 3-(ethoxycarbonyl) propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, in particular 1,1-difluoroalkyl, all of which are straight-chain or branched.

The above-mentioned alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In another preferred embodiment of the present invention, $R^{1-4}$ are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

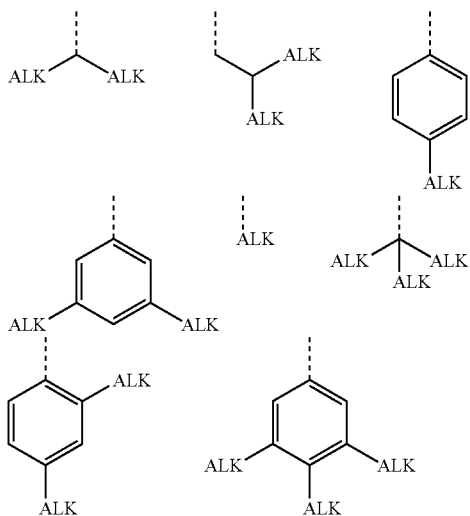

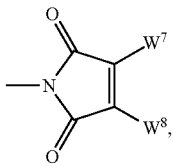

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

—$CY^1$=$CY^2$— is preferably —CH=CH—, —CF=CF— or —CH=C(CN)—.

Halogen is F, Cl, Br or I, preferably F, Cl or Br.

—CO—, —C(=O)— and —C(O)— denote a carbonyl group, i.e.

The compounds, units and polymers according to the present invention may also be substituted with a polymerisable or crosslinkable reactive group, which is optionally protected during the process of forming the polymer. Particular preferred units polymers of this type are those comprising one or more units of formula I wherein one or more of $R^{1-4}$ denote or contain a group P-Sp-. These units and polymers are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or crosslinkable group P is selected from $CH_2$=$CW^1$—C(O)—O—, $CH_2$=$CW^1$—C(O)—,

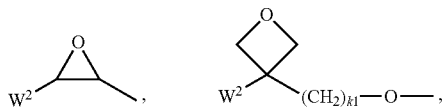

$CH_2$=$CW^2$—(O)$_{k1}$—, $CW^1$=CH—C(O)—(O)$_{k3}$—, $CW^1$=CH—C(O)—NH—, $CH_2$=$CW^1$—C(O)—NH—, $CH_3$—CH=CH—O—, ($CH_2$=CH)$_2$CH—OC(O)—, ($CH_2$=CH—$CH_2$)$_2$CH—O—C(O)—, ($CH_2$=$CH)_2$CH—O—, ($CH_2$=CH—$CH_2$)$_2$N—, ($CH_2$=CH—$CH_2$)$_2$N—C(O)—, HO—$CW^2W^3$—, HS—$CW^2W^3$—, $HW^2$N—, HO—$CW^2W^3$—NH—, $CH_2$=CH—(C(O)—O)$_{k1}$-Phe-(O)$_{k2}$—, $CH_2$=CH—(C(O))$_{k1}$-Phe-(O)$_{k2}$—, Phe-CH=CH—, HOOC—, OCN—, and $W^4W^5W^6$Si—, with $W^1$ being H, F, Cl, CN, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, $k_1$, $k_2$ and $k_3$ being independently of each other 0 or 1, $k_3$ preferably being 1, and $k_4$ being an integer from 1 to 10.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—C(O)—O—, $CH_2$=C($CH_3$)—C(O)—O—, $CH_2$=CF—C(O)—O—, $CH_2$=CH—O—, ($CH_2$=CH)$_2$CH—O—C(O)—, ($CH_2$=CH)$_2$CH—O—,

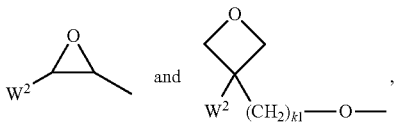

or protected derivatives thereof. Further preferred groups P are selected from the group consisting of vinyloxy, acrylate, methacrylate, fluoroacrylate, chloracrylate, oxetan and epoxy groups, very preferably from an acrylate or methacrylate group.

Polymerisation of group P can be carried out according to methods that are known to the ordinary expert and described in the literature, for example in D. J. Broer; G. Challa; G. N. Mol, *Macromol. Chem*, 1991, 192, 59.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —C(O)—, —C(O)O—, —OC(O)—, —OC(O)—O—, —S—C(O)—, —C(O)—S—, —CH═CH— or —C≡C— in such a manner that O and/or S atoms are not linked directly to one another, X' is —O—, —S—, —C(O)—, —C(O)O—, —OC(O)—, —O—C(O)O—, —C(O)—NR$^O$—, —NR$^O$—C(O)—, —NR$^O$—C(O)—NR$^{OO}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH═N—, —N═CH—, —N═N—, —CH═CR$^O$—, —CY$^1$═CY$^2$—, —C≡C—, —CH═CH—C(O)O—, —OC(O)—CH═CH— or a single bond, R$^O$ and R$^{OO}$ are independently of each other H or alkyl with 1 to 12 C-atoms, and Y$^1$ and Y$^2$ are independently of each other H, F, Cl or CN.

X' is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH═N—, —N═CH—, —N═N—, —CH═CR$^O$—, —CY$^1$═CY$^2$—, —C≡C— or a single bond, in particular —O—, —S—, —C≡C—, —CY$^1$═CY$^2$— or a single bond. In another preferred embodiment X' is a group that is able to form a conjugated system, such as —C≡C— or —CY$^1$═CY$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S— CH$_2$CH$_2$— or —CH$_2$CH$_2$—NH—CH$_2$CH$_2$— or —(SiR$^O$R$^{OO}$—O)$_p$—, with p being an integer from 2 to 12, q being an integer from 1 to 3 and R$^O$ and R$^{OO}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

If R$^1$ and/or R$^2$ in formula I denote substituted aryl or heteroaryl, it is preferably substituted by one or more groups L, wherein L is selected from P-Sp-, F, Cl, Br, I, —OH, —CN, —NO$_2$, —NCO, —NCS, —OCN, —SCN, —C(═O)NR$^O$R$^{OO}$, —C(═O)X$^0$, —C(═O)R$^O$, —NR$^O$R$^{OO}$, C(═O)OH, optionally substituted aryl or heteroaryl having 4 to 20 ring atoms, or straight chain, branched or cyclic alkyl with 1 to 20, preferably 1 to 12 C atoms wherein one or more non-adjacent CH$_2$ groups are optionally replaced, in each case independently from one another, by —O—, —S—, —NR$^O$—, —SiR$^O$R$^{OO}$—, —C(═O)—, —C(═O)O—, —CY$^1$═CY$^2$— or —C≡C— in such a manner that O and/or S atoms are not linked directly to one another and which is unsubstituted or substituted with one or more F or Cl atoms or OH groups, and X$^0$ is halogen, preferably F, Cl or Br, and Y$^1$, Y$^2$, R$^O$ and R$^{OO}$ have the meanings given above and below.

Preferably R$^1$ and R$^2$ denote straight-chain, branched or cyclic alkyl with 1 to 30 C atoms which is unsubstituted or substituted by one or more F atoms.

Further preferably R$^1$ and R$^2$ together with the sp$^2$-hybridised C atom of the alkylidene group form a cyclic group with 1 to 20 C atoms, preferably 1 to 10 C atoms, which is unsubstituted or substituted by one or more F atoms or by one or more C$_1$-C$_{10}$ alkyl groups.

Preferably R$^1$ and R$^2$ do not contain a difluorinated C atom in α-position to the sp$^2$-hybridised C atom of the alkylidene group.

Further preferably one of R$^1$ and R$^2$ is H and the other is different from H, and is preferably straight-chain, branched or cyclic alkyl with 1 to 30 C atoms which is unsubstituted or substituted by one or more F atoms.

Further preferably R$^1$ and/or R$^2$ are independently of each other selected from the group consisting of aryl and heteroaryl, each of which is optionally fluorinated, alkylated or alkoxylated and has 4 to 30 ring atoms.

The compounds according to the present invention include small molecules, monomers, oligomers and polymers.

Oligomers and polymers according to the present invention preferably comprise one or more units of formula I as defined above and below.

Preferred polymers according to the present invention comprise one or more repeating units of formula II:

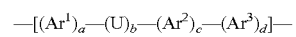

wherein

U is a unit of formula I,

Ar$^1$, Ar$^2$, Ar$^3$ are, on each occurrence identically or differently, and independently of each other, aryl or heteroaryl that is different from U, preferably has 5 to 30 ring atoms, and is optionally substituted, preferably by one or more groups R$^S$, R$^S$ is on each occurrence identically or differently F, Br, Cl, —CN, —NC, —NCO, —NCS, —OCN, —SCN, —C(O)NR$^O$R$^{OO}$, —C(O)X$^0$, —C(O)R$^O$, —NH$_2$, —NR$^O$R$^{OO}$, —SH, —SR$^O$, —SO$_3$H, —SO$_2$R$^O$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, R$^O$ and R$^{OO}$ are independently of each other H or optionally substituted C$_{1-40}$ carbyl or hydrocarbyl, and preferably H or alkyl with 1 to 12 C-atoms, P is a polymerisable or crosslinkable group, Sp is a spacer group or a single bond, X$^0$ is halogen, preferably F, Cl or Br, a, b and c are on each occurrence identically or differently 0, 1 or 2, d is on each occurrence identically or differently 0 or an integer from 1 to 10, wherein the polymer comprises at least one repeating unit of formula II wherein b is at least 1.

Further preferred polymers according to the present invention comprise, in addition to the units of formula I or II, one or more repeating units selected from monocyclic or polycyclic aryl or heteroaryl groups that are optionally substituted.

These additional repeating units are preferably selected of formula III

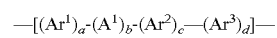 III wherein Ar$^1$, Ar$^2$, Ar$^3$, a, b, c and d are as defined in formula II, and A$^1$ is an aryl or heteroaryl group that is different from U and Ar$^{1-3}$, preferably has 5 to 30 ring atoms, is optionally substituted by one or more groups R$^S$ as defined above and below, and is preferably selected from aryl or heteroaryl groups having electron acceptor properties, wherein the polymer comprises at least one repeating unit of formula III wherein b is at least 1.

R$^S$ preferably has one of the meanings given for R$^1$.

The conjugated polymers according to the present invention are preferably selected of formula IV:

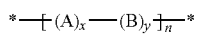  IV wherein
A is a unit of formula I,
B is a unit that is different from A and comprises one or more aryl or heteroaryl groups that are optionally substituted, and is preferably selected of formula III,
x is >0 and 1,
y is ≥0 and <1,
x+y is 1, and
n is an integer>1.

Preferred polymers of formula IV are selected of the following formulae

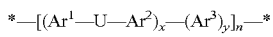  IVa

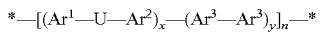  IVb

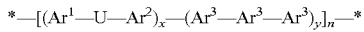  IVc

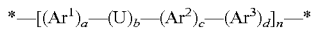  IVd

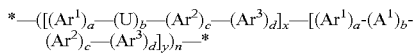  IVe wherein U, $Ar^1$, $Ar^2$, $Ar^3$, a, b, c and d have in each occurrence identically or differently one of the meanings given in formula II, $A^1$ has on each occurrence identically or differently one of the meanings given in formula III, and x, y and n are as defined in formula IV, wherein these polymers can be alternating or random copolymers, and wherein in formula IVd and IVe in at least one of the repeating units $[(Ar^1)_a—(U)_b—(Ar^2)_c—(Ar^3)_d]$ and in at least one of the repeating units $[(Ar^1)_a-(A^1)_b-(Ar^2)_c—(Ar^3)_d]$ b is at least 1.

In the polymers according to the present invention, the total number of repeating units n is preferably from 2 to 10,000. The total number of repeating units n is preferably 5, very preferably 10, most preferably 50, and preferably 500, very preferably 1,000, most preferably 2,000, including any combination of the aforementioned lower and upper limits of n.

The polymers of the present invention include homopolymers and copolymers, like statistical or random copolymers, alternating copolymers and block copolymers, as well as combinations thereof.

Especially preferred are polymers selected from the following groups:
Group A consisting of homopolymers of the unit U or $(Ar^1—U)$ or $(Ar^1—U—Ar^2)$ or $(Ar^1—U—Ar^3)$ or $(U—Ar^2—Ar^3)$ or $(Ar^1—U—Ar^2—Ar^3)$, i.e. where all repeating units are identical,
Group B consisting of random or alternating copolymers formed by identical units $(Ar^1—U—Ar^2)$ and identical units $(Ar^3)$,
Group C consisting of random or alternating copolymers formed by identical units $(Ar^1—U—Ar^2)$ and identical units $(A^1)$,
Group D consisting of random or alternating copolymers formed by identical units $(Ar^1—U—Ar^2)$ and identical units $(Ar^1-A^1-Ar^2)$,
wherein in all these groups U, D', $Ar^1$, $Ar^2$ and $Ar^3$ are as defined above and below, in groups A, B and C $Ar^1$, $Ar^2$ and $Ar^3$ are different from a single bond, and in group D one of $Ar^1$ and $Ar^2$ may also denote a single bond.

Further preferred are copolymers selected from the group consisting of the following subformulae

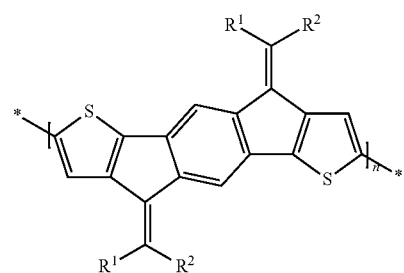  IV1

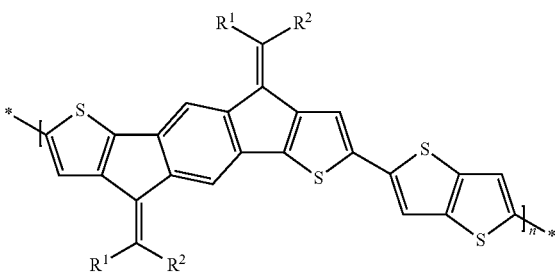  IV2

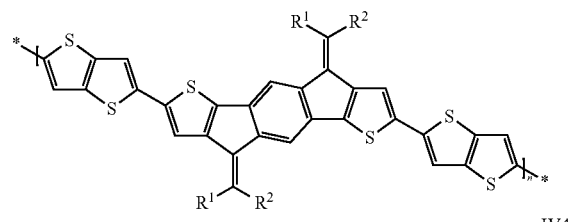  IV3

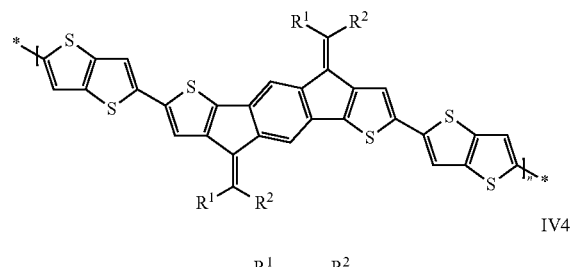  IV4

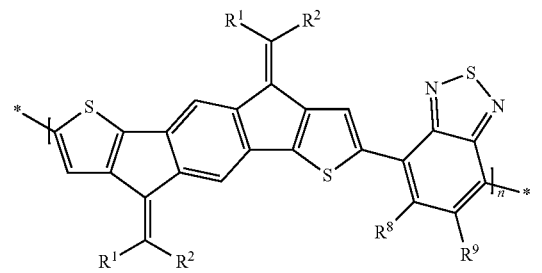  IV5

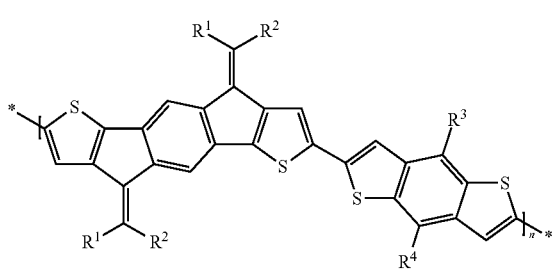

wherein $R^1$ and $R^2$ and n have independently of each other, and on each occurrence identically or differently, one of the meanings as given in formula I and IV, and $R^3$ and $R^4$ have independently of each other one of the meanings as given for $R^1$ above and below.

Preferred polymers of formulae IV, IVa-IVe and IV1-IV5 are selected of formula V R⁵-chain-R⁶     V wherein "chain" denotes a polymer chain of formulae IV, IVa-IVe or IV1-IV5, and R⁵ and R⁶ have independently of each other one of the meanings of R¹ as defined above, or denote, independently of each other, H, F, Br, Cl, I, —CH₂Cl, —CHO, —CR$^a$=CR$^b$₂, —SiR$^a$R$^b$R$^c$, —SiR$^a$X'X", —SiR$^a$R$^b$X', —SnR$^a$R$^b$R$^c$, —BR$^a$R$^b$, —B(OR$^a$)(OR$^c$), —B(OH)₂, —O—SO₂—R$^a$, —C≡CH, —C≡C—SiR$^a$₃, —ZnX', —Sn(Z⁴)₃, an endcap group, or P-Sp-, wherein P and Sp are as defined above, X' and X" denote halogen, R$^a$, R$^b$ and R$^c$ independently of each other denote H or alkyl with 1 to 20 C atoms, and two of R$^a$, R$^b$ and R$^c$ may also form an aliphatic ring together with the hetero atom to which they are attached, and Z⁴ is selected from the group consisting of alkyl and aryl, each being optionally substituted.

Preferred endcap groups R⁵ and R⁶ are H, $C_{1-20}$ alkyl, or optionally substituted $C_{6-12}$ aryl or $C_{2-10}$ heteroaryl, very preferably H or phenyl.

In the polymers represented by formulae IV, IVa-IVe, IV1-IV5 and V, x denotes the mole fraction of units A, y denotes the mole fraction of units B, and n denotes the degree of polymerisation or total number of units A and B. These formulae includes block copolymers, random or statistical copolymers and alternating copoymers of A and B, as well as homopolymers of A for the case when x is >0 and y is 0.

Monomers according to the present invention preferably comprise a unit of formula I as defined above and below, and one or more reactive functional groups which are attached to the unit of formula I and which can be reacted to form a polymer.

Preferably the monomers are selected of formula VI

R⁵—Ar¹—U—Ar²—R⁶     VI wherein U, Ar¹, Ar², R⁵ and R⁶ have the meanings of formula II and V, or one of the preferred meanings as described above and below, and preferably at least one of R⁵ and R⁶ is different from H and is preferably a reactive group.

Especially preferred are monomers of formula VI wherein R⁵ and R⁶ are, preferably independently of each other, selected from the group consisting of Cl, Br, I, O-tosylate, O-triflate, O-mesylate, O-nonaflate, —SiMe₂F, —SiMeF₂, —O—SO₂Z¹, —B(OZ²)₂, —CZ³=C(Z³)₂, —C≡CH, —C≡CSi(Z¹)₃, —ZnX⁰ and —Sn(Z⁴)₃, wherein X⁰ is halogen, preferably Cl, Br or I, $Z^{1-4}$ are selected from the group consisting of alkyl and aryl, each being optionally substituted, and two groups Z² may also together form a cyclic group.

Small molecule compounds according to the present invention are preferably selected of formula VII

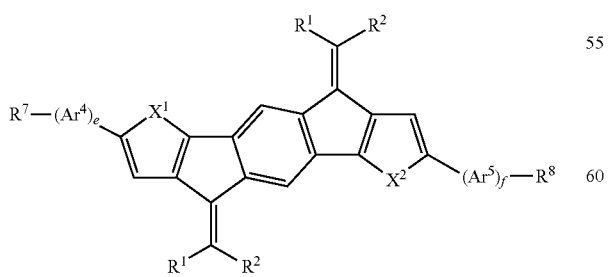

VII wherein R¹, R², X¹ and X² are as defined in formula I, Ar⁴, Ar⁵ independently of each other and on each occurrence identically or differently have one of the meanings of Ar¹ or Ar³ as given in formula II or one of their preferred meanings given above and below, R⁷, R⁸ independently of each other denote H, F, Br, Cl, —CN, —NC, —NCO, —NCS, —OCN, —SCN, —C(O)NR⁰R⁰⁰, —C(O)X⁰, —C(O)R⁰, —C(O)OR⁰, —O—C(O)R⁰, —NH₂, —NR⁰R⁰⁰, —SH, —SR⁰, —SO₃H, —SO₂R⁰, —OH, —NO₂, —CF₃, —SF₅, P-Sp-, or optionally substituted silyl, carbyl or hydrocarbyl with 1 to 40 C atoms that is optionally substituted and optionally comprises one or more hetero atoms, and wherein one or more C atoms are optionally replaced by a hetero atom, and R⁰, R⁰⁰ and X⁰ are as defined in formula II, and e and f independently of each other denote 0, 1, 2 or 3.

Preferably R⁷ and R⁸ denote H, F or straight chain or branched alkyl or fluoroalkyl with 1 to 20 C atoms.

Especially preferred are compounds of formula VIIa

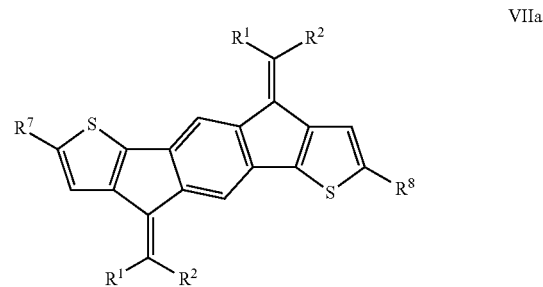

VIIa wherein R¹, R², R⁷ and R⁸ are as defined above and below. Very preferred are compounds of formula VIIa wherein R⁷ and R⁸ are H or F.

Especially preferred are repeating units, monomers, polymers and small molecules of formulae I, II, III, IV, IVa-IVe, IV1-IV5, V, VI, VII and VIIa and their subformulae, wherein one or more of Ar¹, Ar² and Ar³ denote aryl or heteroaryl, preferably having electron donor properties, selected from the group consisting of the following formulae

(D1)

(D2)

(D3)

(D4)

-continued
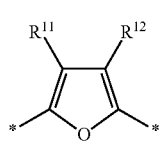 (D5)
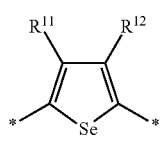 (D6)
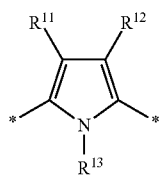 (D7)
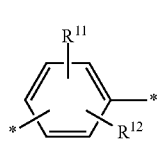 (D8)
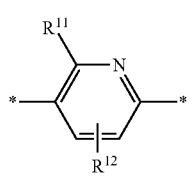 (D9)
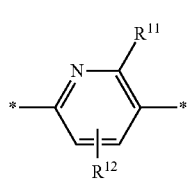 (D10)
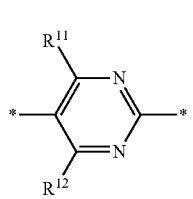 (D11)
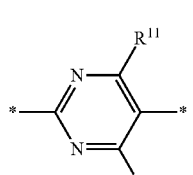 (D12)
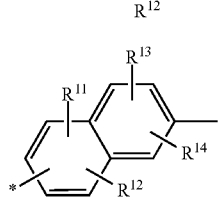 (D13)
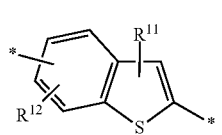 (D14)
-continued
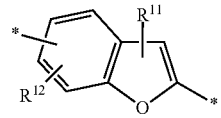 (D15)
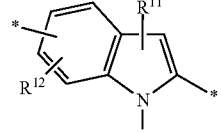 (D16)
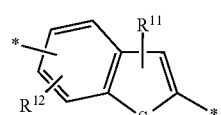 (D17)
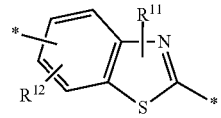 (D18)
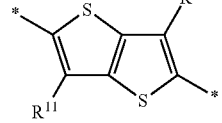 (D19)
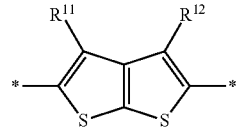 (D20)
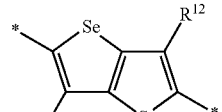 (D21)
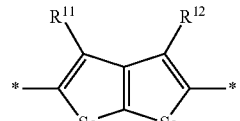 (D22)
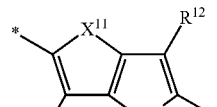 (D23)
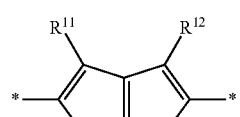 (D24)
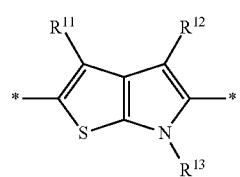 (D25)

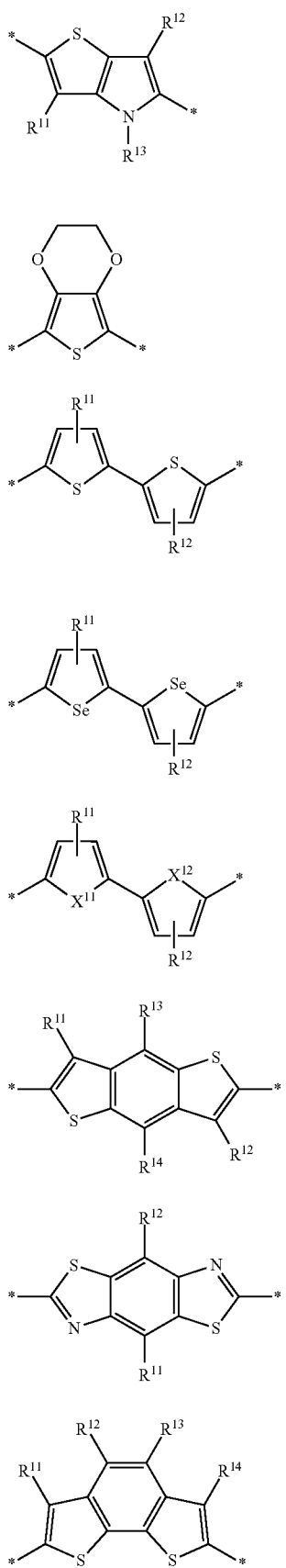

-continued
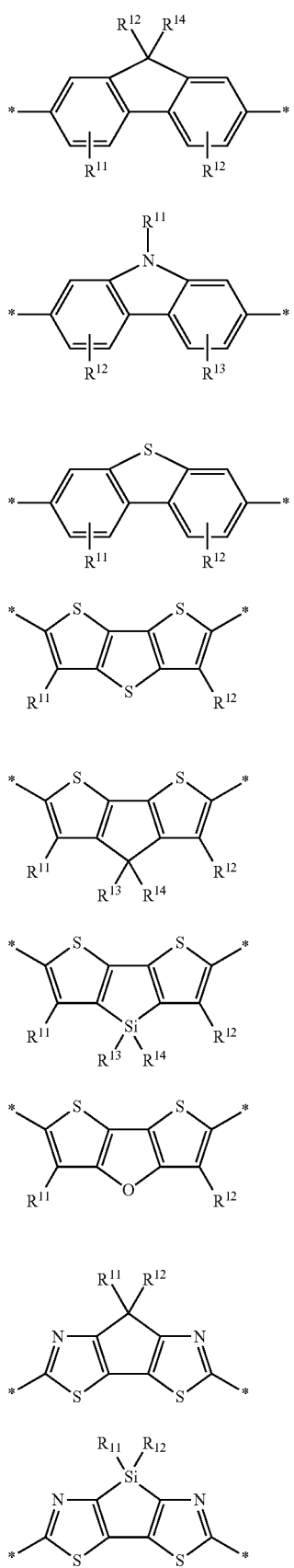
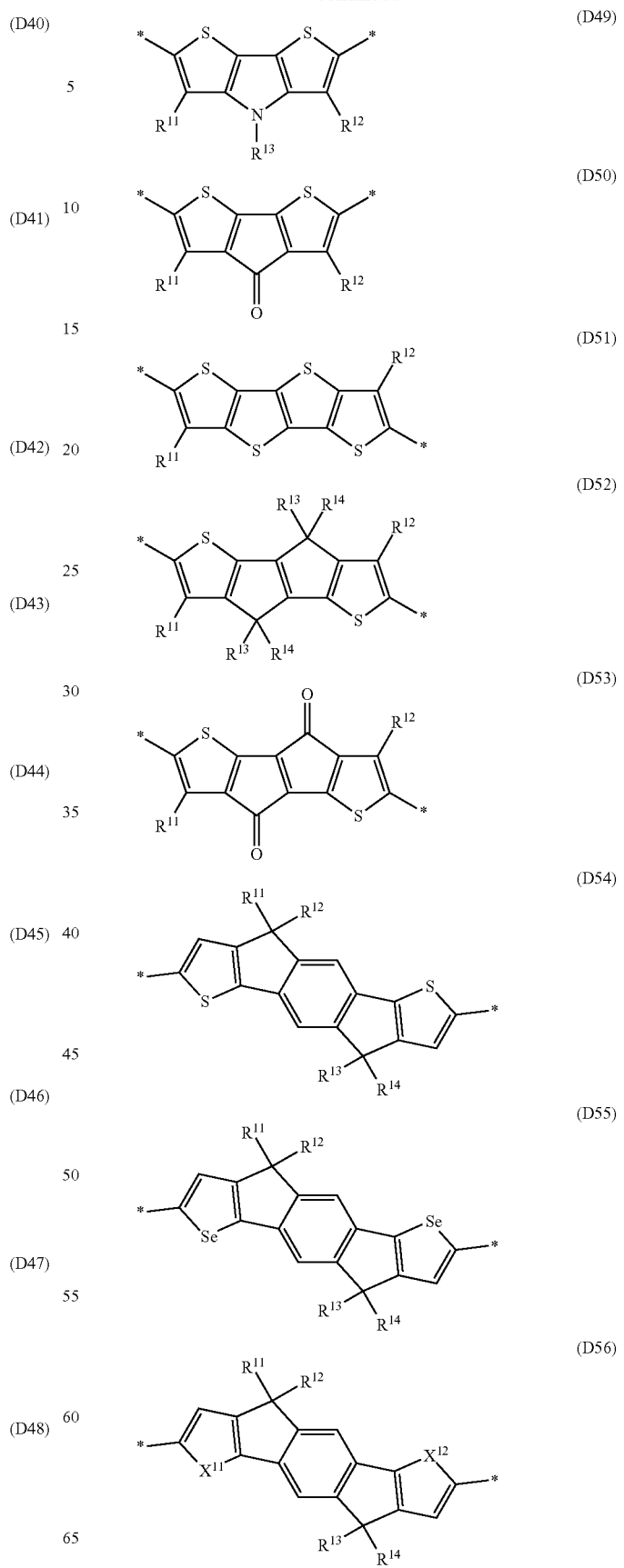

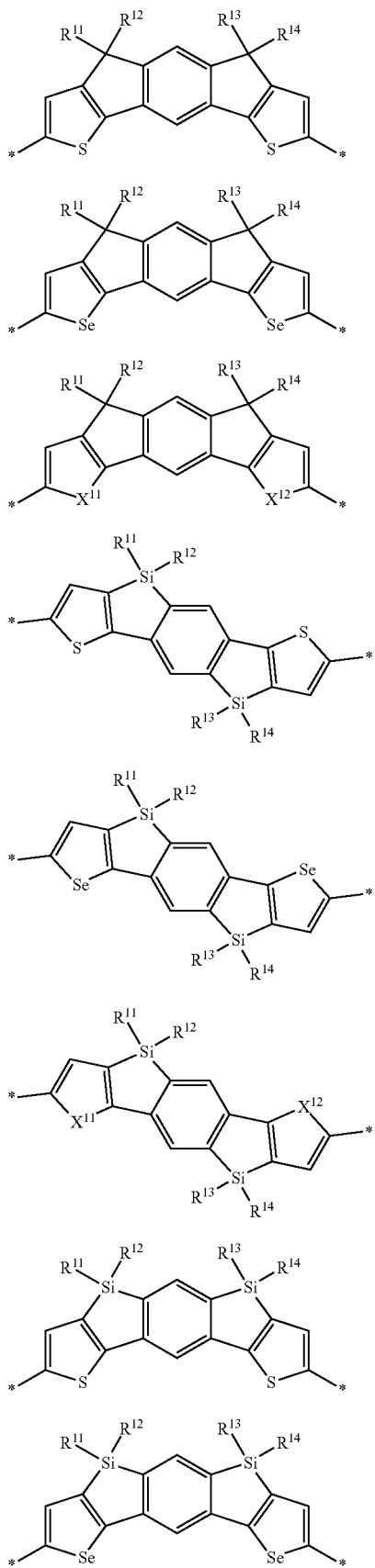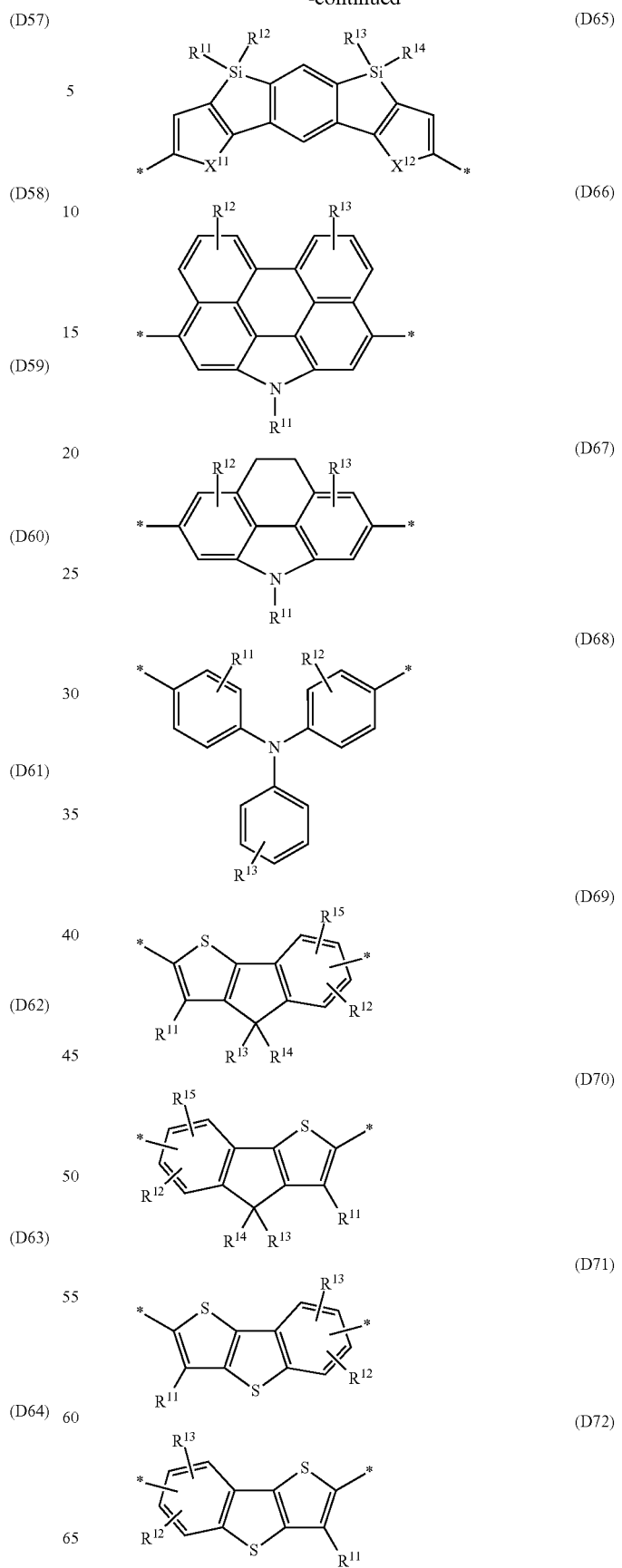

-continued
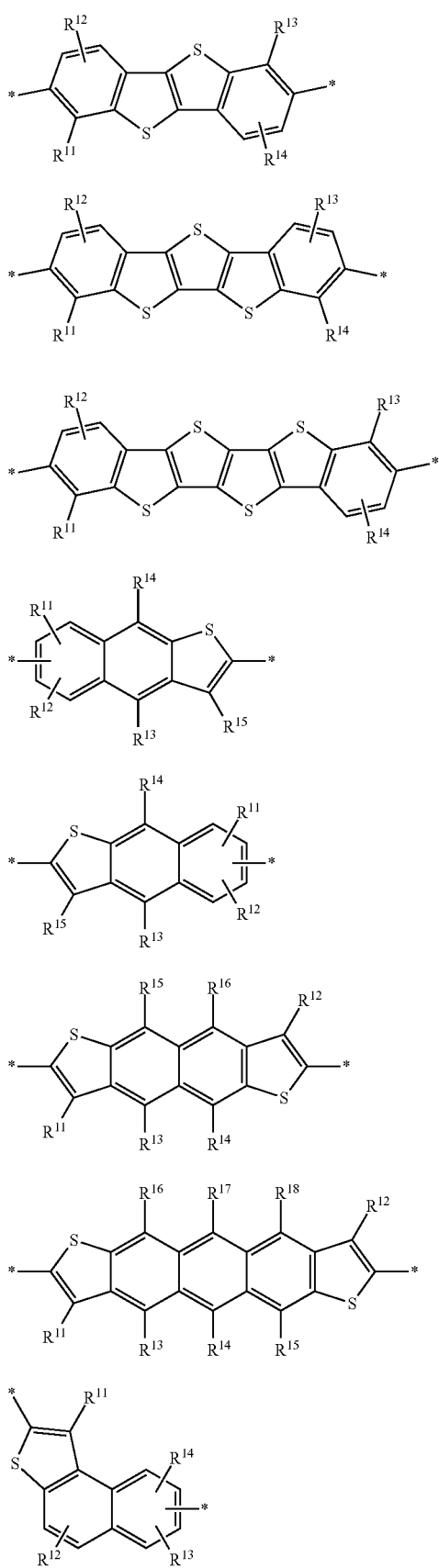
(D73)
(D74)
(D75)
(D76)
(D77)
(D78)
(D79)
(D80)
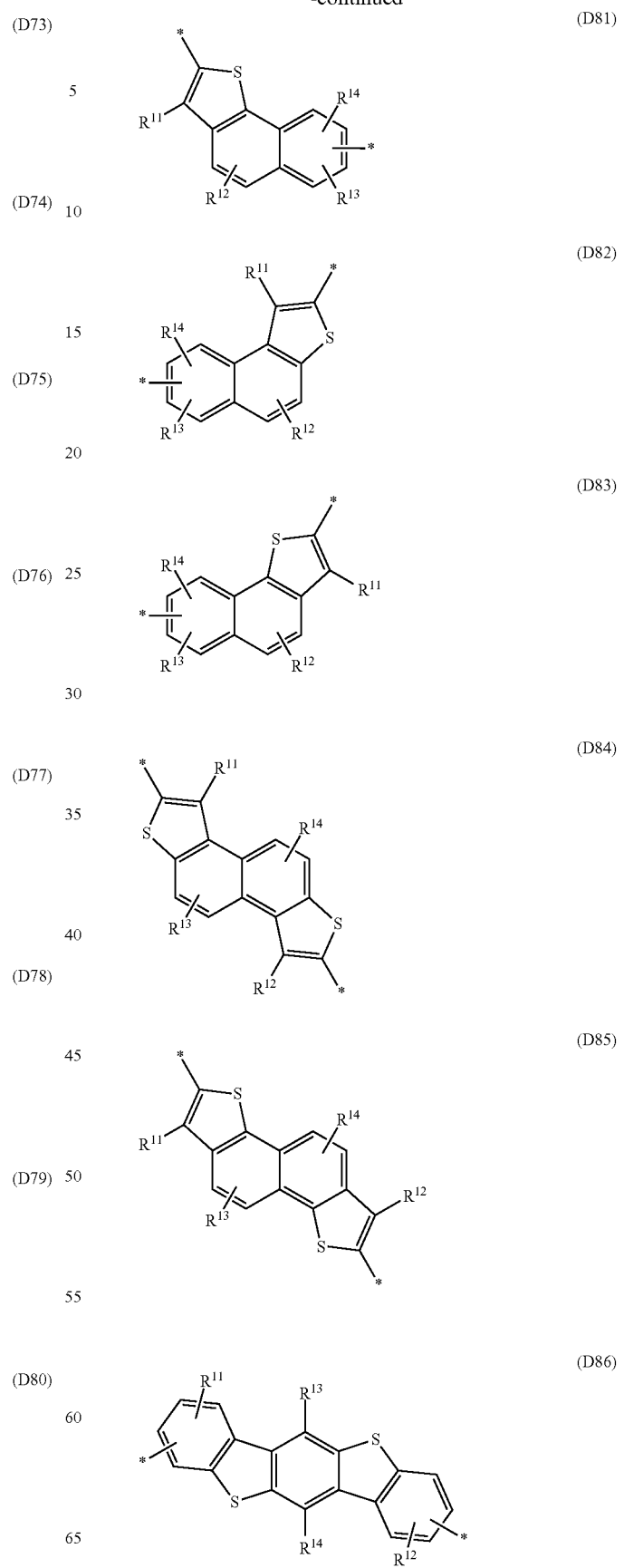
(D81)
(D82)
(D83)
(D84)
(D85)
(D86)

(D87)
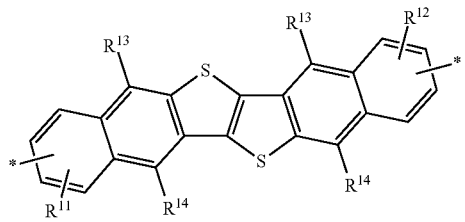

(D88)
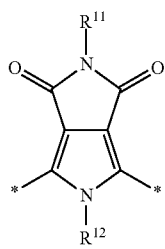

wherein one of $X^{11}$ and $X^{12}$ is S and the other is Se, and $R^{11}$, $R^{12}$, $R^{13}$, $R^{14}$, $R^{15}$, $R^{16}$, $R^{17}$ and $R^{18}$ independently of each other denote H or have one of the meanings of R as defined above and below.

Especially preferred are repeating units, monomers, polymers and small molecules of formulae I, II, III, IV, IVa-IVe, IV1-IV5, V, VI, VII and VIIa and their subformulae, wherein one or more of $Ar^3$ and $A^1$ denote aryl or heteroaryl, preferably having electron acceptor properties, selected from the group consisting of the following formulae (A1)
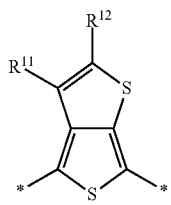

(A2)
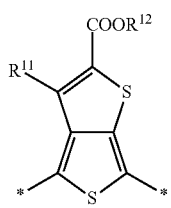

(A3)
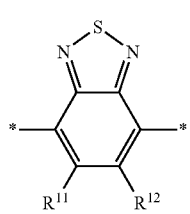

(A4)
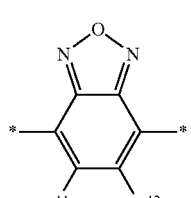

(A5)
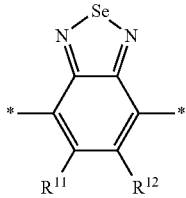

(A6)
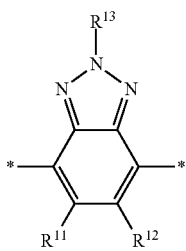

(A7)
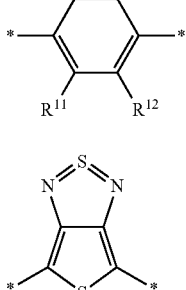

(A8)
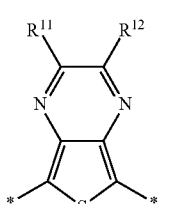

(A9)
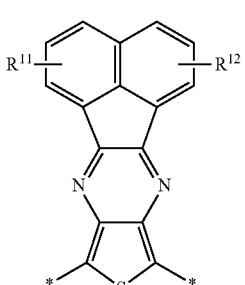

(A10)
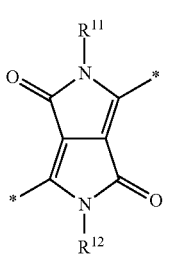

(A11)
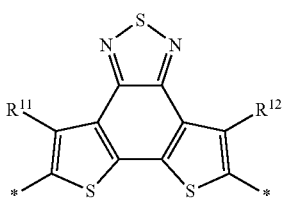

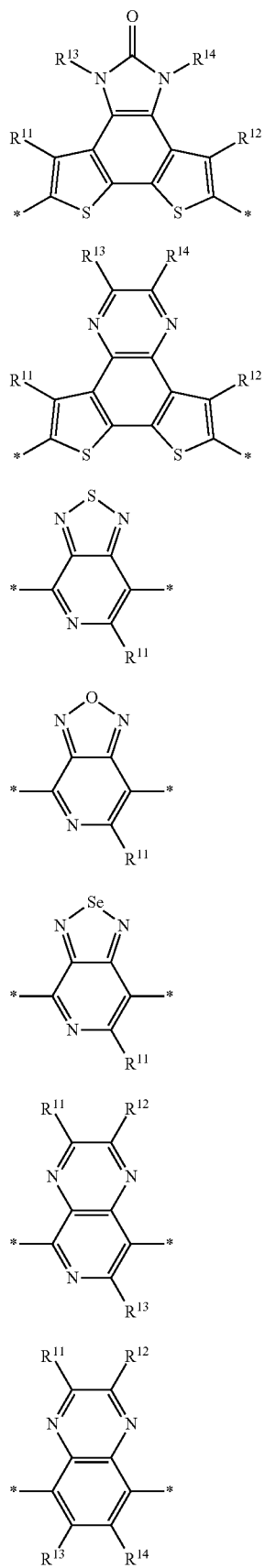
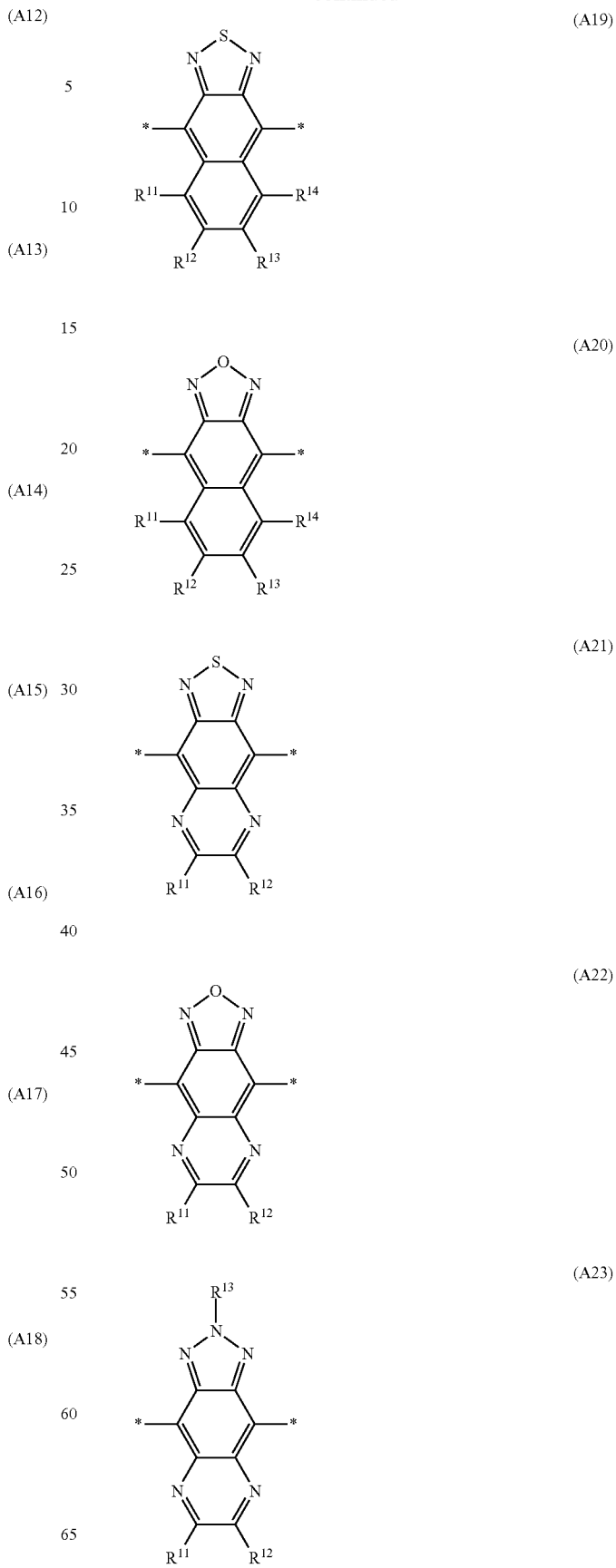

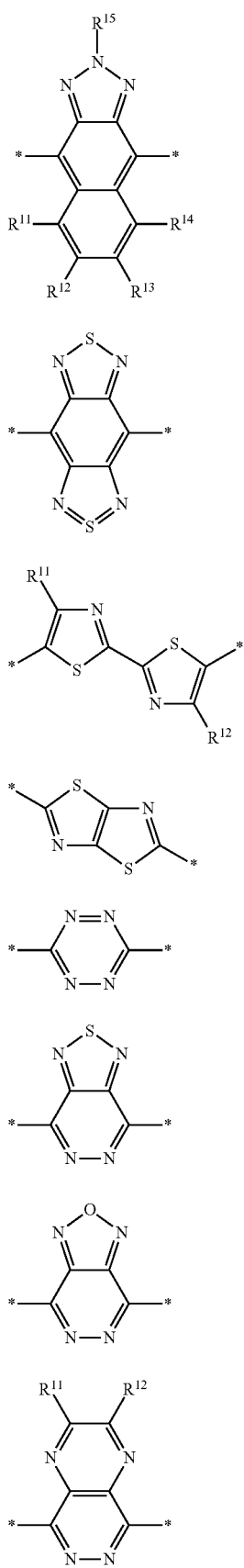
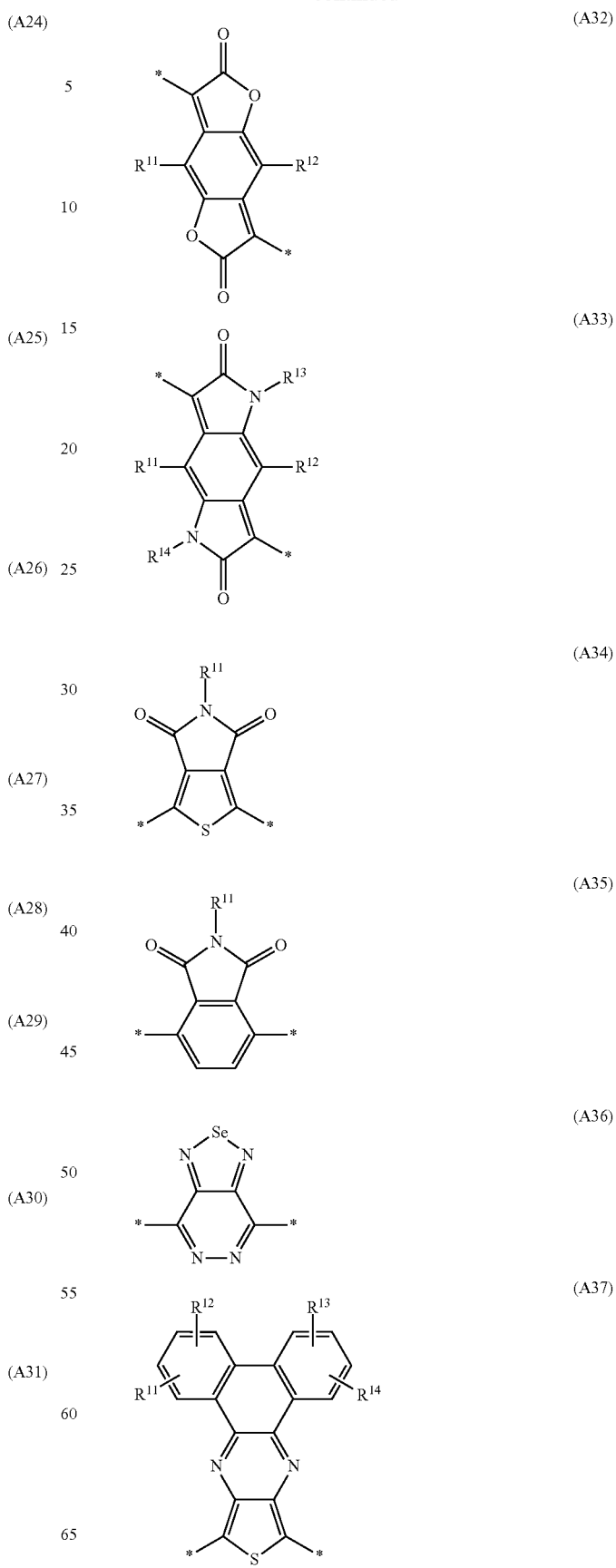

-continued

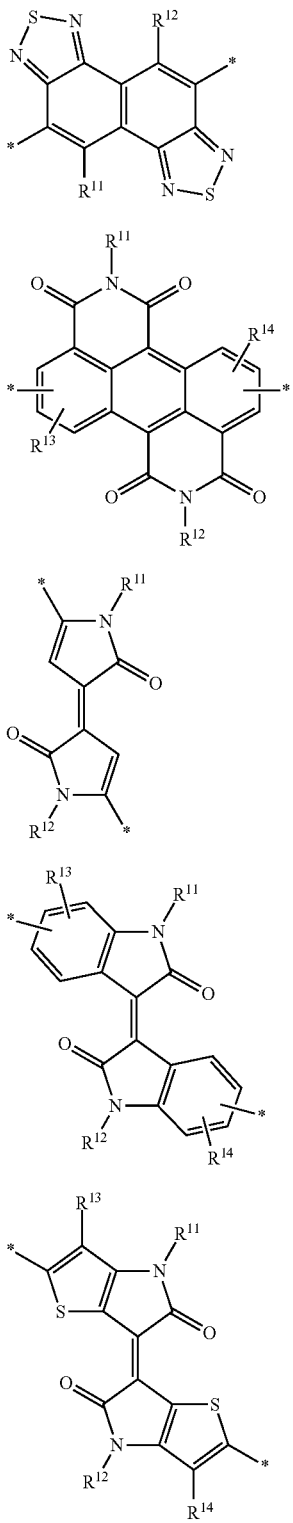

(A38)

(A39)

(A40)

(A41)

(A42)

wherein one of $X^{11}$ and $X^{12}$ is S and the other is Se, and $R^{11}$, $R^{12}$, $R^{13}$, $R^{14}$ and $R^{15}$ independently of each other denote H or have one of the meanings of R as defined above and below.

Very preferred are compounds, repeating units, monomers and polymers of formulae I, IA, II, III, IV, IVa-IVe, IV1-IV5, V, VI, VII, VIIa and their subformulae selected from the following list of preferred embodiments:

y is ≥0 and 1,
b=d=1 and a=c=0, preferably in all repeating units,
a=b=c=d=1, preferably in all repeating units,
a=b=d=1 and c=0, preferably in all repeating units,
a=b=c=1 and d=0, preferably in all repeating units,
a=c=2, b=1 and d=0, preferably in all repeating units,
a=c=2 and b=d=1, preferably in all repeating units,
n is at least 5, preferably at least 10, very preferably at least 50, and up to 2,000, preferably up to 500.
$M_w$ is at least 5,000, preferably at least 8,000, very preferably at least 10,000, and preferably up to 300,000, very preferably up to 100,000,
$X^1$ and $X^2$ are S,
$X^1$ and $X^2$ are Se,
$X^1$ and $X^2$ are O,
$X^1$ and $X^2$ are Te,
$X^1$ and $X^2$ are CH=CH,
one of $R^1$ and $R^2$ is H and the other is different from H,
$R^1$ and $R^2$ are different from H,
$R^1$ and/or $R^2$ are independently of each other selected from the group consisting of primary alkyl with 1 to 30 C atoms, secondary alkyl with 3 to 30 C atoms, and tertiary alkyl with 4 to 30 C atoms, wherein in all these groups one or more H atoms are optionally replaced by F,
$R^1$ and $R^2$ together with the alkylidene C atom form a cyclic group with 1 to 20, preferably 1 to 10 C atoms, which is unsubstituted or substituted by one or more F atoms or by one or more $C_1$-$C_{10}$ alkyl groups,
$R^1$ and/or $R^2$ are independently of each other selected from the group consisting of aryl and heteroaryl, each of which is optionally fluorinated, alkylated or alkoxylated and has 4 to 30 ring atoms,
$R^1$ and/or $R^2$ are independently of each other selected from the group consisting of primary alkoxy or sulfanylalkyl with 1 to 30 C atoms, secondary alkoxy or sulfanylalkyl with 3 to 30 C atoms, and tertiary alkoxy or sulfanylalkyl with 4 to 30 C atoms, wherein in all these groups one or more H atoms are optionally replaced by F,
$R^1$ and/or $R^2$ are independently of each other selected from the group consisting of aryloxy, heteroaryloxy, each of which is optionally alkylated or alkoxylated and has 4 to 30 ring atoms,
$R^1$ and/or $R^2$ are independently of each other selected from the group consisting of alkylcarbonyl, alkoxycarbonyl and alkylcarbonyloxy, all of which are straight-chain or branched, are optionally fluorinated, and have from 1 to 30 C atoms,
$R^3$ and/or $R^4$ are independently of each other selected from the group consisting of primary alkyl with 1 to 30 C atoms, secondary alkyl with 3 to 30 C atoms, and tertiary alkyl with 4 to 30 C atoms, wherein in all these groups one or more H atoms are optionally replaced by F,
$R^3$ and/or $R^4$ are independently of each other selected from the group consisting of primary alkoxy or sulfanylalkyl with 1 to 30 C atoms, secondary alkoxy or sulfanylalkyl with 3 to 30 C atoms, and tertiary alkoxy or sulfanylalkyl with 4 to 30 C atoms, wherein in all these groups one or more H atoms are optionally replaced by F,
$R^3$ and/or $R^4$ are independently of each other selected from the group consisting of alkylcarbonyl, alkoxycarbonyl and alkylcarbonyloxy, all of which are straight-chain or branched, are optionally fluorinated, and have from 1 to 30 C atoms,
$R^0$ and $R^{00}$ are selected from H or $C_1$-$C_{10}$-alkyl,
$R^5$ and $R^6$ are selected from H, halogen, —CH$_2$Cl, —CHO, —CH=CH$_2$—SiR'R"R'", —SnR'R"R'", —BR'R", —B(OR')(OR"), —B(OH)$_2$, P-Sp, $C_1$-$C_{20}$- alkyl, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl, $R^5$ and $R^6$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^4$)$_2$, —C≡CH and —Sn(Z$^4$)$_3$, wherein $Z^{1-4}$ are selected from the group consisting of alkyl and aryl, each being optionally substituted, and two groups $Z^2$ may also form a cyclic group, very preferably from Br, $R^7$ and $R^8$ denote H, $R^7$ and/or $R^8$ denote F, e and f are 0.

The polymers of the present invention can be synthesized according to or in analogy to methods that are known to the skilled person and are described in the literature. Other synthesis methods can be taken from the examples. For example, the polymers can be suitably prepared by aryl-aryl coupling reactions, such as Yamamoto coupling, Suzuki coupling, Stille coupling, Sonogashira coupling, Heck coupling or Buchwald coupling. Suzuki coupling and Yamamoto coupling are especially preferred.

The small molecules, and the monomers which are polymerised to form the repeat units of the polymers, can be prepared according to methods which are known to the person skilled in the art.

Preferably the polymers are prepared from monomers of formula VI or its preferred embodiments as described above and below.

Another aspect of the invention is a process for preparing a polymer by coupling one or more identical or different monomeric units of formula I or monomers of formula VI with each other and/or with one or more comonomers in a polymerisation reaction, preferably in an aryl-aryl coupling reaction.

Suitable and preferred comonomers are selected from the following formulae $R^5$—Ar$^3$—R$^6$          C1

$R^5$-A$^1$-R$^6$          C2 wherein Ar$^3$ has one of the meanings of formula II or one of the preferred meanings given above and below, $A^1$ has one of the meanings of formula III or one of the preferred meanings given above and below, and $R^5$ and $R^6$ have one of the meanings of formula V different from H, and preferably denote reactive functional groups like for example halogen, stannyl and boronate groups as defined in formula V.

Preferred methods for polymerisation are those leading to C—C-coupling or C—N-coupling, like Suzuki polymerisation, as described for example in WO 00/53656, Yamamoto polymerisation, as described in for example in T. Yamamoto et al., *Prog. Polym. Sci.*, 1993, 17, 1153-1205 or in WO 2004/022626 A1, and Stille coupling. For example, when synthesizing a linear polymer by Yamamoto polymerisation, monomers as described above having two reactive halide groups $R^5$ and $R^6$ is preferably used. When synthesizing a linear polymer by Suzuki polymerisation, preferably a monomer as described above is used wherein at least one reactive group $R^5$ or $R^6$ is a boronic acid or boronic acid derivative group.

Suzuki polymerisation may be used to prepare homopolymers as well as statistical, alternating and block random copolymers. Statistical or block copolymers can be prepared for example from the above monomers of formula V wherein one of the reactive groups $R^5$ and $R^6$ is halogen and the other reactive group is a boronic acid or boronic acid derivative group. The synthesis of statistical, alternating and block copolymers is described in detail for example in WO 03/048225 A2 or WO 2005/014688 A2.

Suzuki polymerisation employs a Pd(0) complex or a Pd(II) salt. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol)$_4$. Preferred Pd(II) salts include palladium acetate, i.e. Pd(OAc)$_2$. Suzuki polymerisation is performed in the presence of a base, for example sodium carbonate, potassium phosphate or an organic base such as tetraethylammonium carbonate. Yamamoto polymerisation employs a Ni(0) complex, for example bis(1,5-cyclooctadienyl) nickel(0).

As alternatives to halogens as described above, leaving groups of formula —O—SO$_2$Z$^1$ can be used wherein $Z^1$ is as described above. Particular examples of such leaving groups are tosylate, mesylate and triflate.

Especially suitable and preferred synthesis methods of the repeating units, monomers, and polymers of formula I, II, III, IV, V and VI are illustrated in the synthesis schemes shown hereinafter, wherein $R^1$, $R^2$, $R^3$, $R^4$ and n are as defined in formula I, II, IV and IV5, and R is an alkyl group.

A preferred synthesis of 4,9-dialkylidene-s-indaceno[1,2-b:5,6-b']dithiophene is exemplarily shown in Scheme 1 below. s-Indaceno[1,2-b:5,6-b']dithiophene 1, synthesized according to literature as disclosed in WO2010/020329 A1 and Zhang et al., *J. Am. Chem. Soc.*, 2010, 132(33), 11437, is suspended in anhydrous tetrahydrofuran. Aldehyde or ketone is added followed by the addition of potassium tert-butoxide solution. The mixture is stirred at a temperature depending on the structures of the carbonyl compounds to yield the corresponding 4,9-dialkylidene-s-indaceno[1,2-b:5,6-b']dithiophenes.

Scheme 1

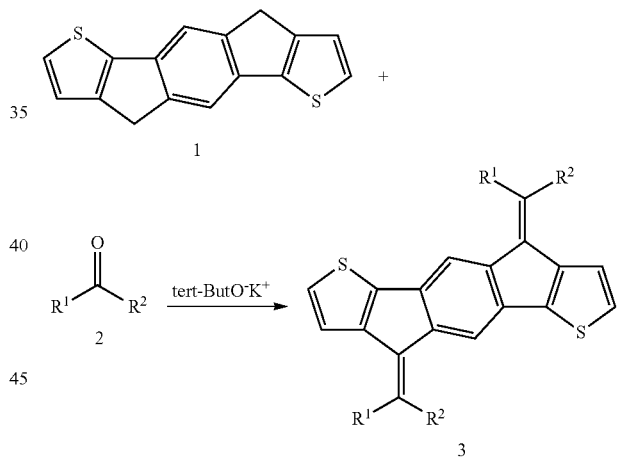

The bromination of 4,9-dialkylidene-s-indaceno[1,2-b:5,6-b']dithiophenes can be achieved by reacting the target molecules with N-bromosuccinimde in dichloromethane as exemplarily shown in Scheme 2.

Scheme 2

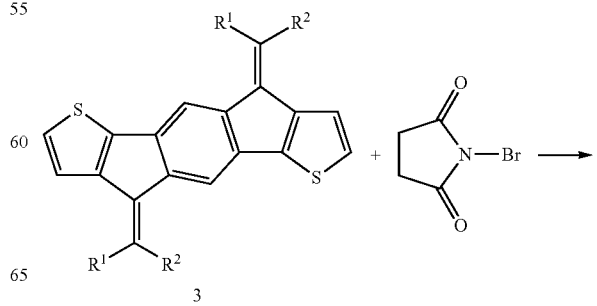

-continued

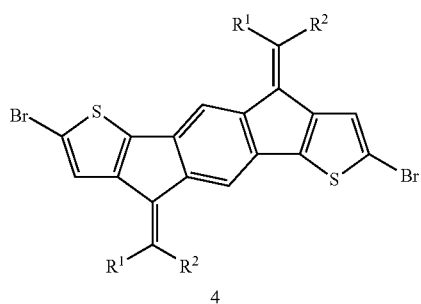

4

The corresponding 2,7-bis(trimethylstannyl)-4,9-dialkylidene-s-indaceno[1,2-b:5,6-b']dithiophene derivatives 4' can be synthesized by lithiation of 3 or 4 with n-butyllithium followed by treating the lithiated species with trimethyltin chloride, as exemplarily shown in Scheme 3.

Scheme 3

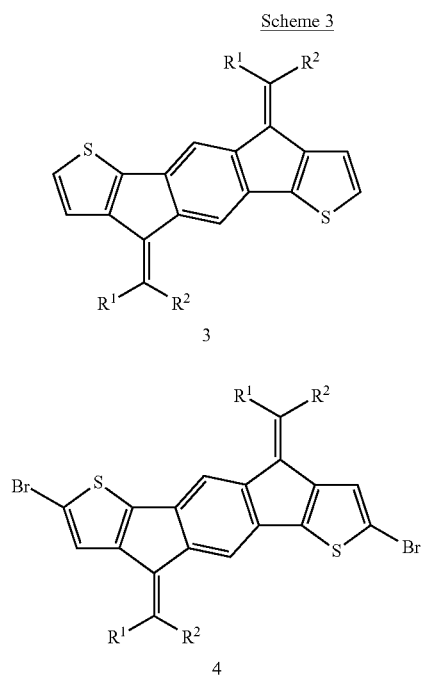

A preferred synthesis of a monomer 5 comprising a unit of formula I and two typical donor units, such as thieno[3,2-b]thiophene, is exemplarily illustrated in Scheme 4.

Scheme 4

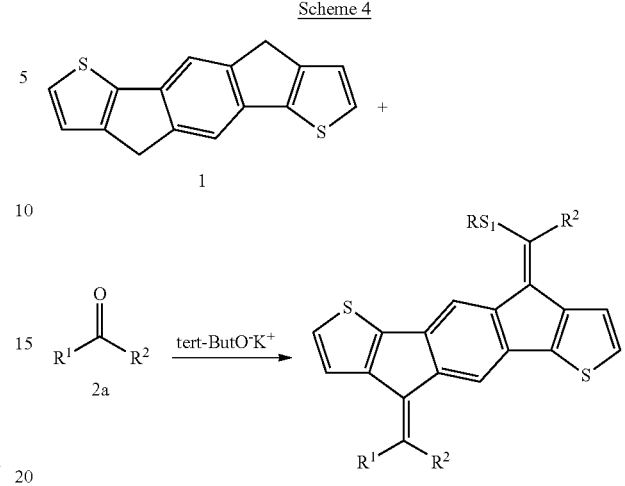

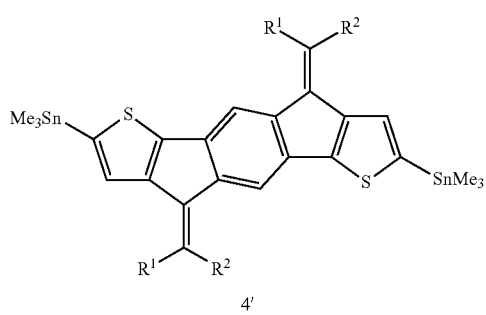

Corresponding monomers comprising a unit of formula I and e.g. two thiophene units or one benzodithiophene unit can be prepared in analogy to Scheme 4.

The homopolymerisation of monomer 4 is illustrated in Scheme 5.

Scheme 5

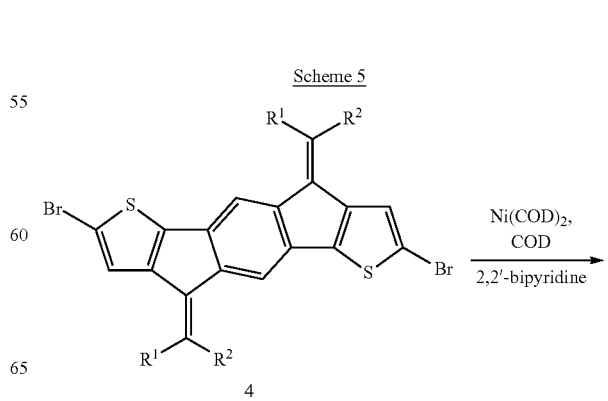

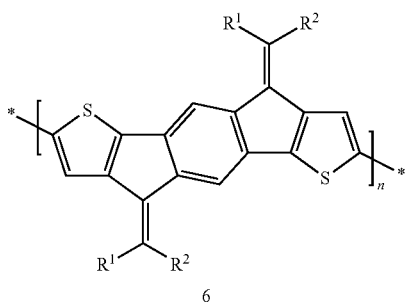

6

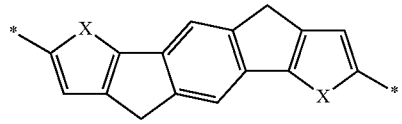

wherein X is S, O, Se, Te or CH=CH, with an aldehyde or ketone of formula IX

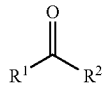

IX wherein $R^1$ and $R^2$ have the meanings given in formula I or one of the preferred meanings given above and below, in a Knoevenagel condensation under alkaline conditions, to give a dialkylidene-s-indacenodiheteroarene, and optionally further comprising the step of adding functional halogen, trialkylstannyl or boronate groups at 2- and 7-position of the product of the previous step by i) halogenation with N-halosuccinimide or elemental halogen, or ii) by lithiation with alkyllithium and lithium amide, followed by reaction with a halogenation reagent, an alkyl borate, a trialkylstannyl chloride or zink chloride.

The term "alkaline conditions" includes, without limitation, reaction in the presence of a metal alkoxide, metal hydroxide, cyclic or acyclic amine or nitrogen containing heteroarene, metal amides or ammonium and alkylammonium hydroxide.

In formula IX very preferably $R^1$ and $R^2$ denote straight-chain, branched or cyclic alkyl with 1 to 20 C atoms which is unsubstituted or substituted by one or more F atoms, or $R^1$ and $R^2$ denote aryl or heteroaryl, each of which is optionally fluorinated, alkylated or alkoxylated and has 4 to 30 ring atoms, or one of $R^1$ and $R^2$ denotes H and the other is selected from the aforementioned alkyl, aryl or heteroaryl groups, or $R^1$ and $R^2$ together with the carbonyl group form a cyclic group with 1 to 20 C atoms, which is unsubstituted or substituted by one or more F atoms or by one or more $C_1$-$C_{10}$ alkyl groups.

The compound and polymers according to the present invention can also be used in mixtures or polymer blends, for example together with monomeric compounds or together with other polymers having charge-transport, semi-conducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

The copolymerisation of monomer 4 or 4' with a typical acceptor unit $Ar^3$ or $A^1$, such as 4,7-bis(4,4,5,5-tetramethyl-[1,3,2]dioxaborolan-2-yl)-benzo[1,2,5]thiadiazole, is exemplarily illustrated in Scheme 6.

Scheme 6

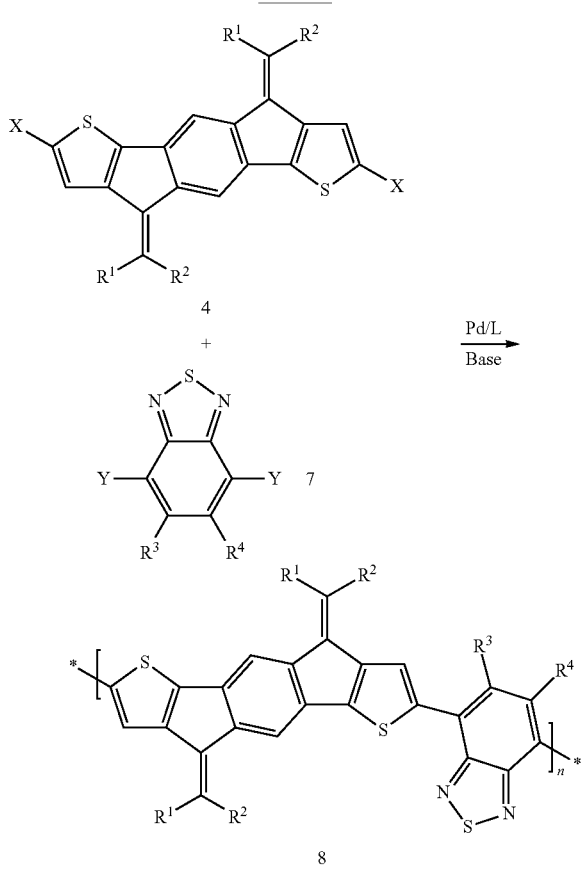

The novel methods of preparing monomers and polymers as described above and below are another aspect of the invention.

Another aspect of the invention is a method of preparing a compound of formula VI or VII as described above and below, comprising the step of reacting an indacenodiarene of formula VIII Another aspect of the invention relates to a formulation comprising one or more small molecules, polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxy-benzene, 1-methylnaphthalene, N-methylpyrrolidinone, 3-fluorobenzotrifluoride, benzotrifluoride, benzotrifluoride, diosane, trifluoromethoxy-benzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the compounds or polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The compounds and polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, dip coating, curtain coating, brush coating, slot dye coating or pad printing.

Ink-jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points>100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound or polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point>100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymer blends and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The compounds and polymers to the present invention are useful as charge transport, semiconducting, electrically conducting, photoconducting or light emitting materials in optical, electrooptical, electronic, electroluminescent or photoluminescent components or devices. In these devices, the polymers of the present invention are typically applied as thin layers or films.

Thus, the present invention also provides the use of the semiconducting compound, polymer, polymers blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a compound, polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a compound, polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV devices the compound or polymer according to the present invention is preferably used as photoactive layer. This implies the use in a formulation that comprises or contains, more preferably consists essentially of, very preferably exclusively of, a p-type (electron donor) semiconductor and an n-type (electron acceptor) semiconductor. The p-type semiconductor is constituted by a compound, preferably a polymer according to the present invention. The n-type semiconductor can be an inorganic material such as zinc oxide or cadmium selenide, or an organic material such as a fullerene derivate, for example (6,6)-phenyl-butyric acid methyl ester derivatized methano $C_{60}$ fullerene, also known as "PCBM" or "$C_{60}$PCBM", as disclosed for example in G. Yu, J. Gao, J. C. Hummelen, F. Wudl, A. J. Heeger, Science, 1995, 270, 1789 and having the structure shown below, or an structural analogous compound with e.g. a $C_{70}$ fullerene group ($C_{70}$PCBM), or a polymer (see for example Coakley, K. M. and McGehee, M. D. Chem. Mater., 2004, 16, 4533).

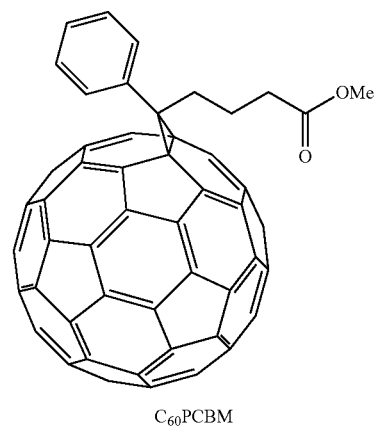 [SMILES: COC(=O)CCCC1(c2ccccc2)C23C=C4Cc5cc6cc7c8c9c(cc%10cc%11c%12c(c%13c%14c%15c(c4c5c4c6c8c(c%154)c4c9c%10c%12c%144)C%1321)C(=C3)C%11)C7]

$C_{60}$PCBM

A blend or mixture of a polymer according to the present invention with a $C_{60}$ or $C_{70}$ fullerene or modified fullerene like $C_{60}$PCBM or $C_{70}$PCBM is the preferred material combination to be used in formulations for OPV devices. Preferably the ratio polymer:fullerene is from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, dip coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the blend or mixture of a polymer according to the present invention with a $C_{60}$ or $C_{70}$ fullerene or modified fullerene like PCBM must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, morpholine, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
  optionally a substrate,
  a high work function electrode, preferably comprising a metal oxide, like for example ITO, serving as anode,
  an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
  a layer, also referred to as "active layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties, for example comprising LiF,
  a low work function electrode, preferably comprising a metal like for example aluminum, serving as cathode,
  wherein at least one of the electrodes, preferably the anode, is transparent to visible light, and
  wherein the p-type semiconductor is a polymer according to the present invention.

A second preferred OPV device according to the invention is an inverted OPV device and comprises the following layers (in the sequence from bottom to top):
  optionally a substrate,
  a high work function metal or metal oxide electrode, comprising for example ITO, serving as cathode,
  a layer having hole blocking properties, preferably comprising a metal oxide like $TiO_x$ or $Zn_x$,
  an active layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
  an optional conducting polymer layer or hole transport layer, preferably comprising an organic polymer or polymer blend, for example of PEDOT:PSS or TBD or NBD,
  an electrode comprising a high work function metal like for example silver, serving as anode,
  wherein at least one of the electrodes, preferably the cathode, is transparent to visible light, and
  wherein the p-type semiconductor is a polymer according to the present invention.

In the OPV devices of the present invent invention the p-type and n-type semiconductor materials are preferably selected from the materials, like the polymer/fullerene systems, as described above When the active layer is deposited on the substrate, it forms a BHJ that phase separate at nanoscale level. For discussion on nanoscale phase separation see Dennler et al, *Proceedings of the IEEE,* 2005, 93 (8), 1429 or Hoppe et al, *Adv. Func. Mater,* 2004, 14(10), 1005. An optional annealing step may be then necessary to optimize blend morphology and consequently OPV device performance.

Another method to optimize device performance is to prepare formulations for the fabrication of OPV(BHJ) devices that may include high boiling point additives to promote phase separation in the right way. 1,8-octanedithiol, 1,8-diiodooctane, nitrobenzene, chloronaphthalene, and other additives have been used to obtain high-efficiency solar cells. Examples are disclosed in J. Peet, et al, *Nat. Mater.,* 2007, 6, 497 or Fréchet et al. *J. Am. Chem. Soc.,* 2010, 132, 7595-7597.

The compounds, polymers, formulations and layers of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound, polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers,
  optionally a substrate.
wherein the semiconductor layer preferably comprises a compound, polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantation of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3\cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913 A1.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad.* Sci. U.S.A., 1999, 96, 12287; D. Wang, X. Gong, P. S. Heeger, F. Rininsland, G. C. Bazan and A. J. Heeger, *Proc. Natl. Acad.* Sci. U.S.A., 2002, 99, 49; N. DiCesare, M. R. Pinot, K. S. Schanze and J. R. Lakowicz, *Langmuir,* 2002, 18, 7785; D. T. McQuade, A. E. Pullen, T. M. Swager, *Chem. Rev.,* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention.

Independent protection may be sought for these features in addition to or alternative to any invention presently claimed.

The invention will now be described in more detail by reference to the following examples, which are illustrative only and do not limit the scope of the invention.

Synthesis of Small Molecules and Monomers

Example 51

In analogy to Scheme 1 the following small molecules were prepared:

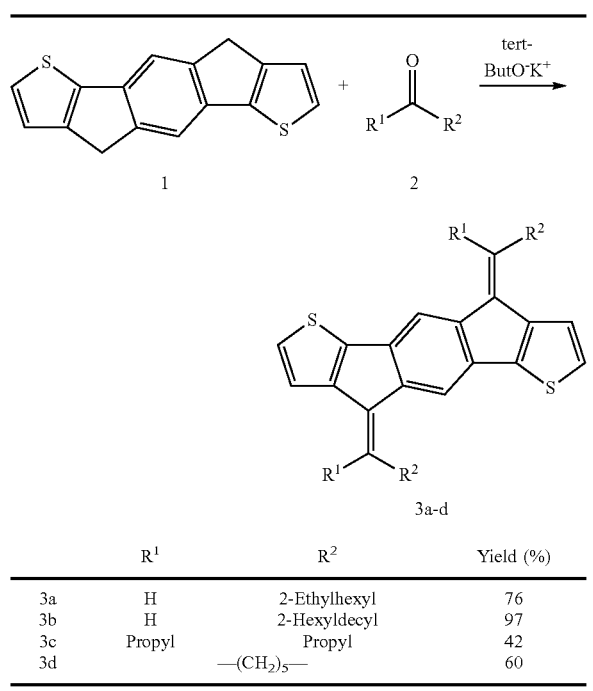

| | R¹ | R² | Yield (%) |
|---|---|---|---|
| 3a | H | 2-Ethylhexyl | 76 |
| 3b | H | 2-Hexyldecyl | 97 |
| 3c | Propyl | Propyl | 42 |
| 3d | —(CH$_2$)$_5$— | | 60 |

4,9-Di(2-hexyldecylidene)-s-indaceno[1,2-b:5,6-b'] dithiophene (3b)

To a suspension of s-indaceno[1,2-b:5,6-b']dithiophene (5.46 g; 20.00 mmol) in anhydrous tetrahydrofuran (100 cm$^3$) was added 2-hexyldecanal (10.58 g; 44.00 mmol). The mixture was degassed by bubbling nitrogen for 20 min. Potassium tert-butoxide solution (1.0M in tert-butanol, 25 cm$^3$; 25.00 mmol) was added dropwise over 15 minutes to yield a brown-yellow solution. The solution was stirred at 22° C. for 17 hours followed by the addition of acetic acid (10 cm$^3$). The solution was concentrated by vacuum evaporation to nearly dryness affording a brown-yellow oily residue. Methanol (100 cm$^3$) was added to the residue and the mixture was left standing for ca. 30 minutes until a dark yellow precipitate was afforded. The solid was suction filtered off and washed with methanol to yield a dark-yellow solid. The solid was purified by flash column chromatography on silica eluted with petroleum ether (40-60° C.) to yield the product as a bright yellow solid (13.78 g, 97%). $^1$H-NMR (CDCl$_3$, 300 MHz): δ=0.85 (m, 6H), 1.22 (m, 10H), 1.46 (m, 2H), 1.62 (m, 2H), 3.03 (m, 1H), 6.36 (d, 9 Hz, 1H), 7.23 (d, 6 Hz, 1H), 7.34 (d, 6 Hz, 1H), 7.85 (s, 1H).

4,9-Di(2-ethylhexylidene)-s-indaceno[1,2-b:5,6-b'] dithiophene (3a)

In analogy to the synthesis of 3b, compound 3a was synthesised from indacenodithiophene (9.55 g; 35.00), THF anhydrous (200 cm$^3$) and 2-ethylhexanal (14.12 ml; 87.50 mmol), and potassium tert-butoxide solution (25 cm$^3$). The crude product was afforded as a deep yellow solid which was purified by a suction filtration through a silica plug washed with cyclohexane followed by a recrystallisation from cyclohexane-ethanol to yield the pure product as yellow crystals (12.90 g, 76%). $^1$HNMR (CDCl$_3$, 300 MHz): δ=0.86 (t, 7.5 Hz, 3H), 0.94 (t, 7.5 Hz, 3H), 1.33 (m, 4H), 1.50 (m, 2H), 1.68 (m, 2H), 2.97 (m, 1H), 6.37 (d, 9 Hz, 1H), 7.25 (d, 6 Hz, 1H), 7.36 (d, 6 Hz, 1H), 7.66 (s, 1H).

4,9-Dicyclohexylidene-s-indaceno[1,2-b:5,6-b']dithiophene (3d)

In analogy to the synthesis of the 3a and 3b, 3d was synthesised from indacenodithiophene (1.50 g; 5.50 mmol), THF anhydrous (30 cm$^3$), and cyclohexanone (2.2 cm$^3$; 21.03 mmol), and potassium tert-butoxide solution (12 cm$^3$; 12.00 mmol). The reaction mixture was stirred at 22° C. for 1 hour then at 60° C. for an additional 2 hours. The crude product was purified by crystallisation from chlorobenzene to afford orange-yellow needles (1.40 g, 60%). $^1$HNMR (o-dichlorobenzene-d$_4$, 300 MHz): δ=1.62 (m, 2H), 1.73 (m, 4H), 2.83 (t, 6 Hz, 2H), 3.00 (t, 6 Hz, 2H), 7.05 (d, 6 Hz, 1H), 7.21 (d, 6 Hz, 1H), 7.87 (s, 1H).

4,9-Di(4-heptylidene)-s-indaceno[1,2-b:5,6-b']dithiophene (3c)

In analogy to the synthesis of the 3a and 3b, compound 3c was synthesised from indacenodithiophene (1.37 g; 5.0 mmol), THF anhydrous (40 cm$^3$), and 4-heptanone (2.14 cm$^3$; 15.00 mmol), and potassium tert-butoxide solution (10 cm$^3$; 10.00 mmol). The reaction mixture was stirred at 60° C. for 4 hour. The crude product was afforded as deep yellow crystals which was purified by a suction filtration through a silica plug washed with cyclohexane followed by a recrystallisation from cyclohexane-ethanol to yield the pure product as deep yellow needles (0.96 g, 42%). ¹HNMR (CDCl₃, 300 MHz): δ=1.10 (t, 7.5 Hz, 3H), 1.18 (t, 7.5 Hz, 3H), 1.74 (m, 4H), 2.68 (m, 2H), 2.78 (m, 2H), 7.23 (s, 2H), 7.68 (s, 1H). ¹³CNMR (CDCl₃, 75 MHz): δ=14.6, 22.0, 22.1, 37.6, 39.7, 115.2, 123.3, 125.7, 129.5, 134.3, 138.3, 142.9, 143.0, 149.6.

Example M1

As described in Scheme 2 the compounds of Example 51 were brominated as follows to give the corresponding monomers:

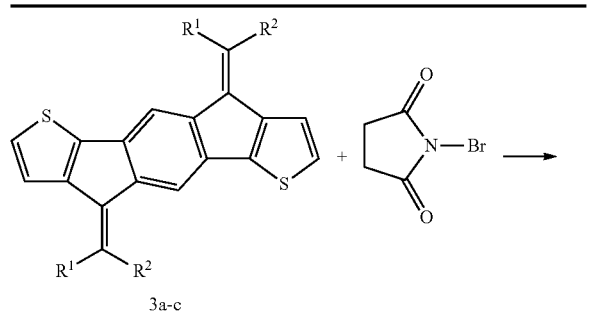

3a-c

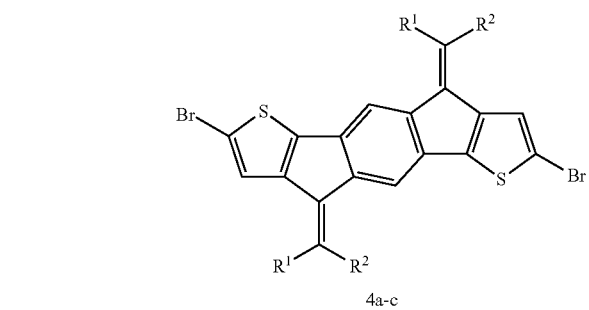

4a-c

| | R1 | R2 | Yield (%) |
|---|---|---|---|
| 4a | H | 2-ethylhexyl | 77 |
| 4b | H | 2-Hexyldecyl | 72 |
| 4c | Propyl | Propyl | 93 |

2,7-Dibromo-4,9-di(2-ethylhexylidene)-s-indaceno[1,2-b:5,6-b']dithiophene (4a)

To a solution of 3a (13.80 g; 28.35 mmol) in anhydrous dichloromethane (300 cm³) at 0° C. was added NBS (15.00 g; 84.28 mmol) in one portion. The mixture was stirred with cooling for 30 minutes to yield a yellow suspension. The cooling bath was removed and the suspension was stirred at 22° C. for an additional 1 hour. The suspension was vacuum evaporated without heating until ca. 50 cm³ of solvent was left. Methanol (200 cm³) was added and the precipitated bright yellow solid was suction filtered off and washed with methanol, then air-dried. The solid was recrystallised from chloroform-ethanol to afford orange-yellow crystals (14.02 g, 77%). ¹HNMR (CDCl₃, 300 MHz): δ=0.86 (t, 7.5 Hz, 3H), 0.93 (t, 7.5 Hz, 3H), 1.30 (m, 4H), 1.48 (m, 2H), 1.68 (m, 2H), 2.85 (m, 1H), 6.36 (d, 8 Hz, 1H), 0.7.35 (s, 1H), 7.56 (s, 1H).

2,7-Dibromo-4,9-di(2-hexyldecylidene)-s-indaceno[1,2-b:5,6-b']dithiophene (4b)

In analogy to the synthesis of 4a, compound 3b (4.27, 6.00 mmol) was brominated with NBS (2.40 g, 13.48 mmol) in dry dichloromethane (200 cm³). The crude product which was bright yellow solid was recrystallised in 2-butanone-isopropanol mixture once and in ethyl acetated once to yield the pure product as yellow crystals (3.90 g, 72%). ¹HNMR (CDCl₃, 300 MHz): δ=0.85 (t, 6 Hz, 6H), 1.22 (m, 20H), 1.45 (m, 2H), 1.61 (m, 2H), 2.92 (m, 1H), 6.36 (d, 9H), 7.34 (m, 1H), 7.55 (s, 1H).

2,7-Dibromo-4,9-di(4-heptylidene)-s-indaceno[1,2-b:5,6-b']dithiophene (4c)

In analogy to the synthesis of 4a-b, compound 3c (0.94 g, 2.05 mmol) was brominated with NBS (1.07 g, 6.00 mmol) in dry dichloromethane (30 cm³). The crude product which was bright yellow crystals was recrystallised in 2-butanone-isopropanol once and in ethyl acetated once to yield the pure product as yellow crystals (1.18 g, 93%). ¹HNMR (CDCl₃, 300 MHz): δ=1.09 (t, 7.5 Hz, 3H), 1.15 (t, 7.5 Hz, 3H), 1.69 (m, 4H), 2.61 (t, 7.5 Hz, 2H), 2.73 (t, 7.5 Hz, 2H), 7.20 (s, 1H), 7.53 (s, 1H).

Example M2

Monomer 4d was prepared as described in Scheme 3:

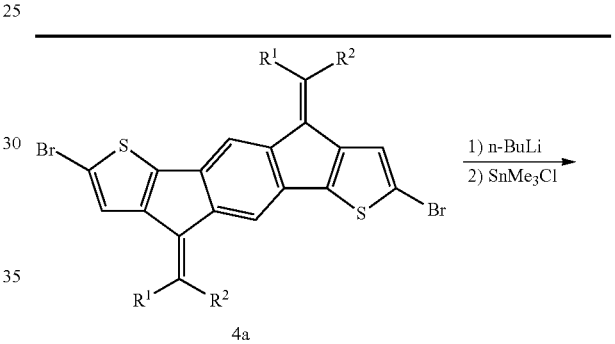

4a

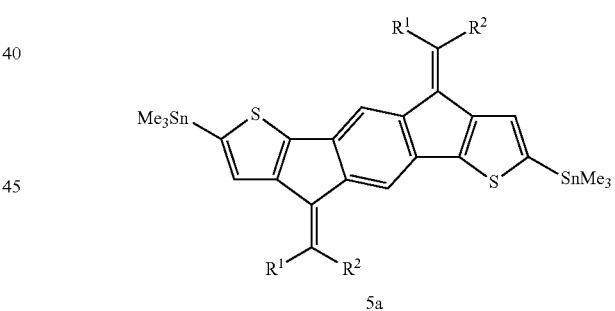

5a

| | R¹ | R² | Yield (%) |
|---|---|---|---|
| 4d | H | 2-Ethylhexyl | 73 |

2,7-Bis(trimethylstannyl)-4,9-di(2-ethylhexylidene)-s-indaceno[1,2-b:5,6-b']dithiophene (4d)

To a yellow suspension of 2,7-dibromo-4,9-di(2-ethylhexylidene)-s-indaceno[1,2-b:5,6-b']dithiophene (4a) (9.77 g; 15.00 mmol) in anhydrous THF (250 cm³) was added n-BuLi (15.2 cm³; 38.00 mmol) over 15 minutes, at −78° C. The resultant blood-red solution was stirred at the low temperature for 1 hour and at −5° C. (ice-acetone bath) for an additional 1 hour to yield a thick red suspension. The suspension was cooled to −78° C. again and trimethyltin chloride (1.0 M in THF, 40 cm³; 40.00 mmol) was added through a syringed quickly and the mixture was stirred at 22° C. for 15 hours to yield a dark-yellow solution. The solution was quenched with NH$_4$Cl solution (100 cm$^3$). The organic layer was separated and aqueous layer was extracted with diethyl ether once (50 cm$^3$). The combined deep yellow ether solution was vacuum evaporated to yield a yellow oil. Methanol (200 cm$^3$) was added slowly with constant shaking to the residue and the yellow precipitate was collected by suction filtration and washed with methanol then air-dried on the filter to yield a yellow powdery solid. The solid was recrystallised three times sequentially from 2-butanone-ethanol, 2-butanone-acetonitrile and ethyl acetate to yield yellow crystals (9.50 g, 73%). $^1$H-NMR (CDCl$_3$, 300 MHz): δ=0.43 (s, 9H), 0.87 (m, 3H), 0.96 (t, 7.5 Hz, 3H), 1.33 (m, 4H), 1.50 (m, 2H), 1.69 (m, 2H), 6.33 (d, 12 Hz, 1H), 7.36 (s, 1H), 7.62 (s, 1H). $^{13}$H-NMR (CDCl$_3$, 75 MHz): δ=−8.1, 12.1, 14.1, 23.0, 28.7, 29.8, 35.4, 41.9, 110.7, 130.0, 132.6, 132.8, 133.8, 139.3, 141.2, 144.6, 151.1.

Example S2

Compounds 5a-c were prepared as described similarly to Scheme 4:

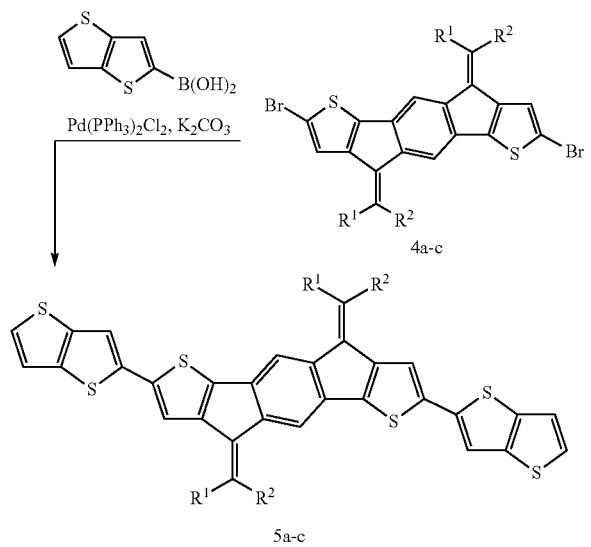

5a: R$^1$ = 2-Ethylhexyl, R$^2$ = H
5c: R$^1$, R$^2$ = Propyl 4,9-Di(2-ethylhexylidene)-2,7-di(thieno[3,2-b]thiophen-2-yl)-s-indaceno[1,2-b:5,6-b']dithiophene The mixture of 2,7-Dibromo-4,9-di(2-ethylhexylidene)-s-indaceno[1,2-b:5,6-b']dithiophene (4a) (0.90 g, 1.40 mmol), thieno[3,2-b]thiophenyl-5-boronic acid (0.77 g, 4.19 mmol) and Pd(PPh$_3$)$_2$Cl$_2$ (42 mg) in THF (40 cm$^3$) was degassed by bubbling nitrogen for 20 minutes followed by the addition of potassium carbonate solution (2.0 M, 4.0 cm$^3$; 8.0 mmol). The deep yellow clear solution was stirred at 70° C. (external) for 24 hours. The dark orange solution was vacuum evaporated to dryness and methanol (50 ml) was added to the residue. The red precipitate was collected by suction filtration and air-dried. The solid was purified by flash-column on silica washed with 5:1 v/v cyclohexane-chloroform mixture to yield the crude product as a scarlet red powdery solid. The solid was crystallised from chloroform-ethanol to yield the product as red crystals 0.35 g (32%). M.p.: 320° C. (DSC). $^1$H-NMR (CDCl$_3$, 300 MHz): δ=0.89 (t, 7.5 Hz, 3H), 0.98 (t, 7.5 Hz, 3H), 1.36 (m, 4H), 1.53 (m, 2H), 1.72 (m, 2H), 2.97 (m, 1H), 6.41 (d, 9 Hz, 1H), 7.22 (d, 4 Hz, 1H), 7.35 (d, 4 Hz, 1H), 7.39 (s, 1H), 7.43 (s, 1H), 7.60 (s, 1H). The structure of the compound was also proved by X-ray single crystal diffraction.

Example M3

4,9-Di(4-heptylidene)-2,7-di(thieno[3,2-b]thiophen-2-yl)-s-indaceno[1,2-b:5,6-b']dithiophene In analogy to the synthesis of Example M3, 2,7-dibromo-4,9-di(4-heptylidene)-s-indaceno[1,2-b:5,6-b']dithiophene (4c) (1.17 g, 1.90 mmol), thieno[3,2-b]thiophenyl-5-boronic acid (1.05 g, 5.69 mmol) and Pd(PPh$_3$)$_2$Cl$_2$ (55 mg), potassium carbonate solution (2.0 M, 6 cm$^3$, 12 mmol) reacted in toluene (40 cm$^3$) for 18 hours at 100° C., to yield the crude product as a rosy red solid. The solid was crystallised from chlorobenzene to afford the pure product as red-brown needles (1.25 g, 89%). $^1$H-NMR (CDCl$_3$, 300 MHz): g=1.14 (t, 7.5 Hz, 3H), 1.19 (t, 7.5 Hz, 3H), 1.77 (m, 4H), 2.72 (t, 7.5 Hz, 2H), 2.81 (t, 7.5 Hz, 2H), 7.20 (d, 4 Hz, 1H), 7.33 (d, 4 Hz, 1H), 7.35 (s, 1H), 7.36 (s, 1H), 7.64 (s, 1H). The structure of the compound was also confirmed by X-ray single crystal analysis.

Synthesis of Polymers

The following polymers were prepared in analogy to Scheme 6:

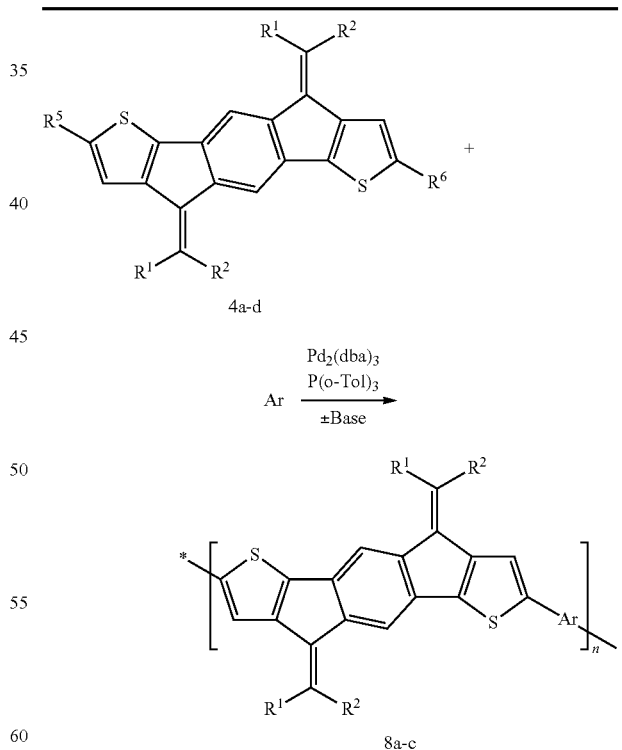

| | R$^1$ | R$^2$ | R$^3$ | R$^4$ | R$^5$ | R$^6$ |
|---|---|---|---|---|---|---|
| 4b | H | 2-Hexyldecyl | — | — | Br | Br |
| 4d | H | 2-Ethylhexyl | — | — | SnMe$_3$ | SnMe$_3$ |
| 7a | — | — | Dodecyloxy | Dodecyloxy | Br | Br |
| 7b | — | — | Octyloxy | Octyloxy | Br | Br |

| | | | | | | |
|---|---|---|---|---|---|---|
| 7c | — | — | H | H | B(OR)₃ | B(OR)₃ |
| 7d | — | — | Dodecyl | Dodecyl | SnMe₃ | SnMe₃ |
| 8a | H | 2-Ethylhexyl | Dodecyloxy | Dodecyloxy | — | — |
| 8b | H | 2-Ethylhexyl | Octyloxy | Octyloxy | — | — |
| 8c | H | 2-Hexyldecyl | H | H | — | — |
| 8d | H | 2-Hexyldecyl | Dodecyl | Dodecyl | — | — |

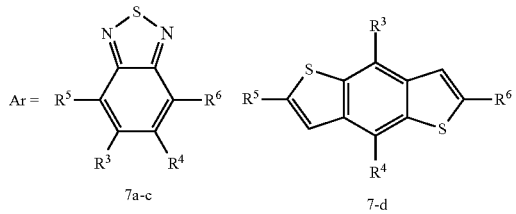

B(OR)₃ = 4,4,5,5-tetramethyl-[1,3,2]dioxaborolanyl

Example P1

Poly[2,7-(4,9-di(2-ethylhexylidene)-s-indaceno[1,2-b:5,6-b']dithiophene)-alt-4,7-(5,6-bis(dodecyloxy)benzo[c][1,2,5]thiadiazole)] (8a) (EHIDT-BT-OC12)

A mixture of 4,7-dibromo-5,6-didodecoxy-2,1,3-benzothiadiazole (7a) (0.663 g; 1.000 mmol), 2,7-bis(trimethylstannyl)-4,9-di(2-ethylhexylidene)-s-indaceno[1,2-b:5,6-b']dithiophene (4d) (0.812 g; 1.000 mmol) and N,N-dimethylformamide, anhydrous (7.5 cm³) in anhydrous toluene (30 cm³) was degassed by bubbling N₂ for 20 minute. Pd₂(dba)₃ (6.5 mg, 1%) and tri(o-tolyl)phosphine (6.9 mg, 2%) were added and the reaction mixture (brownish-yellow suspension) was heated to 100° C. (external) and stirred for 5 hours. The deep-blue viscous solution was poured into stirred methanol (400 cm³). The precipitate was suction filtered and the polymer on the filter was washed each with methanol and acetone once, then air-dried to yield a dark-blue solid. The solid was purified by Soxhlet extracted sequentially with acetone and petroleum ether (40-60° C.). The residual was then dissolved in chloroform and precipitated in methanol. The solid was collected by suction filtration and dried in vacuum at 60° C. for 24 hours to yield the polymer as dark blue solid (0.85 g, 86%). GPC (chlorobenzene, 50° C.): Mn=19,800 g/mol, Mw=44,800 g/mol, Pd=2.27.

Example P2

Poly[2,7-(4,9-di(2-ethylhexylidene)-s-indaceno[1,2-b:5,6-b']dithiophene)-alt-4,7-(5,6-di(octyloxy)benzo[c][1,2,5]thiadiazole)] (8b) (EHIDT-BT-OC8)

In analogous to the synthesis of EHIDT-BT-OC12 (8a), polymer EHIDT-BT-OC8 (8b) was synthesised from 4,7-dibromo-5,6-dioctyloxy-2,1,3-benzothiadiazole (7b) (0.550 g, 1.000 mol), 2,7-bis(trimethylstannyl)-4,9-di(2-ethylhexylidene)-s-indaceno[1,2-b:5,6-b']dithiophene (4d) (0.812 g; 1.000 mmol), Pd₂(dba)₃ (6.5 mg, 1 mol %) and tri(o-tolyl)phosphine (6.9 mg, 2 mol %) in the solvent mixture of N,N-anhydrous dimethylformamide (7.50 cm³) and anhydrous toluene (30 cm³). The yield of the dark blue polymer was (0.73 g, 83%). GPC (chlorobenzene, 50° C.): Mn=13,300 g/mol, Mw=28,200 g/mol, Pd=2.12.

Example P3

Poly[2,7-(4,9-di(2-hexyldecylidene)-s-indaceno[1,2-b:5,6-b']dithiophene)-alt-4,7benzo[c][1,2,5]thiadiazole)] (8c) (HDIDT-BT)

A Schlenk tube was charged with 2,7-dibromo-4,9-di(2-hexyldecylidene)-s-indaceno[1,2-b:5,6-b']dithiophene (4b) (1.303 g, 1.500 mmol), 4,7-Bis-(4,4,5,5-tetramethyl-[1,3,2]dioxaborolan-2-yl)-2,1,3benzothiadiazole (7c) (0.582 g; 1.500 mmol), Pd₂(dba)₃ (27.5 mg; 2.00 mol %), tri(o-tolyl)phosphine (36.5 mg; 8.00 mol %), Aliquat 336 (0.1 g) and anhydrous toluene (50 cm³). The mixture was degassed by bubbling nitrogen for 30 minutes. In the meantime, sodium carbonate solution (1.0M, 10 cm³, 10 mmol) was also degassed and added into the Schlenk tube. The tube was sealed and the reaction mixture was stirred at 120° C. (external) for 24 hours. The dark-blue mixture was poured into vigorously stirred methanol (400 cm³). The precipitate was collected by suction filtration and was washed with methanol and water to yield a purple-blue polymer solid. The solid was purified by Soxhlet extracted sequentially with methanol, acetone, petroleum ether (40-60° C.) and cyclohexane. The residual was then dissolved in chloroform and precipitated in methanol. The solid was collected by suction filtration and dried in vacuum over at 60° C. for 24 hours to yield the polymer as a brown-blue solid (0.89 g, 70%). GPC (chlorobenzene, 50° C.): Mn=14,300 g/mol, Mw=43,300 g/mol, Pd=3.0.

Example P4

Poly[2,7-(4,9-di(2-hexyldecylidene)-s-indaceno[1,2-b:5,6-b']dithiophene)-alt-2,6-(4,8-didodecyl-benzo[1,2-b:4,5-b']dithiophene)] (8d) (HDIDT-BDT-C12)

In analogous to the synthesis of Examples P1 and P2, polymer HDIDT-BDT-C12 (8d) was synthesised from 2,7-dibromo-4,9-di(2-hexyldecylidene)-s-indaceno[1,2-b:5,6-b']dithiophene (4b) (0.869 g, 1.000 mmol), 4,8-didodecyl-2,6-bis(trimethylstannyl) benzo[1,2-b:4,5-b']dithiophene (7d) (0.853 g, 1.000 mmol), Pd₂(dba)₃ (6.5 mg, 1 mol %) and tri(o-tolyl)phosphine (6.9 mg, 2 mol %) in the solvent mixture of N,N-anhydrous dimethylformamide (7.50 cm³) and anhydrous toluene (30 cm³). The crude polymer was purified by Soxhlet extraction with acetone and petroleum ether (40-60° C.) and finally with cyclohexane. The cyclohexane solution was concentrated under vacuum and the residue was dissolved in chloroform then precipitated from methanol. Suction filtration and drying in vacuum oven at 50° C. for 24 hours yielded purple-red polymer solid 1.11 g (90%). GPC (trichlorobenzene, 140° C.): Mn=14,800 g/mol, Mw=45,500 g/mol, Pd=3.1.

Example D1

Transistor Fabrication and Measurement

Top-gate thin-film organic field-effect transistors (OFETs) were fabricated on glass substrates with photolithographically defined Au source-drain electrodes. A 1 wt. % solution of polymer in o-dichlorobenenzene was spin-coated ontop followed by a spin-coated fluoropolymer dielectric material (D139). Finally a photolithographically defined Au gate electrode was deposited. The electrical characterization of the transistor devices was carried out in ambient air atmosphere using computer controlled Agilent 4155C Semiconductor Parameter Analyser. Charge carrier mobilities for polymer examples 8a-d in the saturation regime ($\mu_{sat}$) were calculated and are shown in table 1. Field-effect mobility was calculated in the saturation regime ($V_d > (V_g - V_0)$) using equation (1):

$$\left(\frac{dI_d^{sat}}{dV_g}\right)_{V_d} = \frac{WC_i}{L}\mu^{sat}(V_g - V_0) \quad (1)$$

where W is the channel width, L the channel length, $C_i$ the capacitance of insulating layer, $V_g$ the gate voltage, $V_0$ the turn-on voltage, and $\mu_{sat}$ is the charge carrier mobility in the saturation regime. Turn-on voltage ($V_0$) was determined as the onset of source-drain current.

TABLE 1

Transistor characteristics

| Polymer Example | Saturated mobility ($\mu_{sat}$) |
|---|---|
| 8a | $5 \times 10^{-3}$ cm²/Vs |
| 8b | $7 \times 10^{-3}$ cm²/Vs |
| 8c | $3 \times 10^{-3}$ cm²/Vs |
| 8d | $2 \times 10^{-4}$ cm²/Vs |

The invention claimed is:

1. A compound comprising one or more divalent units of formula I

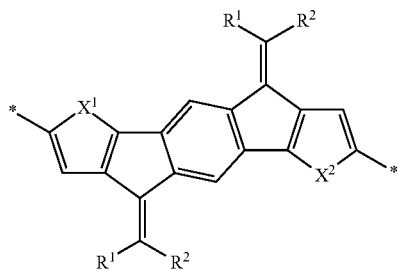

I wherein $X^1$ and $X^2$ are independently of each other O, S, Se, Te or CH=CH, $R^1$ and $R^2$ independently of each other, and on each occurrence identically or differently, denote H, straight-chain, branched or cyclic alkyl, with 1 to 30 C atoms, in which one or more non-adjacent C atoms are optionally replaced by —O—, —S—, —NR$^0$—, —SiR$^0$R$^{00}$—, —CY$^1$=CY$^2$— or —C≡C— in such a manner that O and/or S atoms are not linked directly to one another, and in which one or more H atoms are optionally replaced by F, Cl, Br, or I, or $R^1$ and $R^2$, independently of each other, and on each occurrence identically or differently, denote aryl, heteroaryl, aryloxy or heteroaryloxy with 4 to 20 ring atoms which is optionally substituted, or $R^1$ and $R^2$ together form an alicyclic group with 1 to 20 C atoms, which is optionally fluorinated or alkylated, $Y^1$ and $Y^2$ are independently of each other H, F, Cl or CN,

* represents a linkage to an adjacent unit or group, and $R^0$ and $R^{00}$ are independently of each other H or optionally substituted $C_{1-40}$ carbyl or hydrocarbyl.

2. The compound according to claim 1, that is a polymer comprising one or more units of formula I as defined in claim 1.

3. The compound according to claim 2, that comprises one or more units of formula II —[(Ar$^1$)$_a$—(U)$_b$—(Ar$^2$)$_c$—(Ar$^3$)$_d$]—  II wherein U is a unit of formula I, Ar$^1$, Ar$^2$, Ar$^3$ are, on each occurrence identically or differently, and independently of each other, aryl or heteroaryl that is different from U, and is optionally substituted, optionally by one or more groups R$^S$, R$^S$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, R$^0$ and R$^{00}$ are independently of each other H or optionally substituted $C_{1-40}$ carbyl or hydrocarbyl, P is a polymerizable or crosslinkable group, Sp is a spacer group or a single bond, $X^0$ is halogen, a, b, c are on each occurrence identically or differently 0, 1 or 2, d is on each occurrence identically or differently 0 or an integer from 1 to 10, wherein the polymer comprises at least one repeating unit of formula II wherein b is at least 1.

4. The compound according to claim 3, additionally comprising one or more repeating units selected of formula III —[(Ar$^1$)$_a$-(A$^1$)$_b$-(Ar$^2$)$_c$—(Ar$^3$)$_d$]—  III wherein A$^1$ is an aryl or heteroaryl group that is different from U and Ar$^{1-3}$, has 5 to 30 ring atoms, is optionally substituted by one or more groups R$^S$ and is aryl or heteroaryl groups having electron donor properties, wherein the polymer comprises at least one repeating unit of formula III wherein b is at least 1.

5. The compound according to claim 4, of formula IV:

*—[(A)$_x$—(B)$_y$]$_n$—*  IV wherein

A is a unit of formula I,

B is a unit that is different from A and comprises one or more aryl or heteroaryl groups that are optionally substituted, x is >0 and ≤1, y is ≥0 and <1, x+y is 1, n is an integer>1, and * represents a linkage to an adjacent unit or group.

6. The compound according to claim 5, of the following formulae

*—[(Ar$^1$—U—Ar$^2$)$_x$—(Ar$^3$)$_y$]$_n$—*  IVa

*—[(Ar$^1$—U—Ar$^2$)$_x$—(Ar$^3$—Ar$^3$)$_y$]$_n$—*  IVb

*—[(Ar$^1$—U—Ar$^2$)$_x$—(Ar$^3$—Ar$^3$—Ar$^3$)$_y$]$_n$—*  IVc

*—[(Ar$^1$)$_a$—(U)$_b$—(Ar$^2$)$_c$—(Ar$^3$)$_d$]$_n$—*  IVd or

*—([(Ar$^1$)$_a$—(U)$_b$—(Ar$^2$)$_c$—(Ar$^3$)$_d$]$_x$—
[(Ar$^1$)$_a$-(A$^1$)$_b$-(Ar$^2$)$_c$—(Ar$^3$)$_d$]$_y$)$_n$—*  IVe wherein * represents a linkage to an adjacent unit or group, these polymers can be alternating or random copolymers, and wherein in formula IVd and IVe in at least one of the repeating units [(Ar¹)ₐ—(U)_b—(Ar²)_c—(Ar³)_d] and in at least one of the repeating units [(Ar¹)ₐ-(A¹)_b-(Ar²)_c—(Ar³)_d] b is at least 1.

7. The compound according to claim 6, of the following formulae

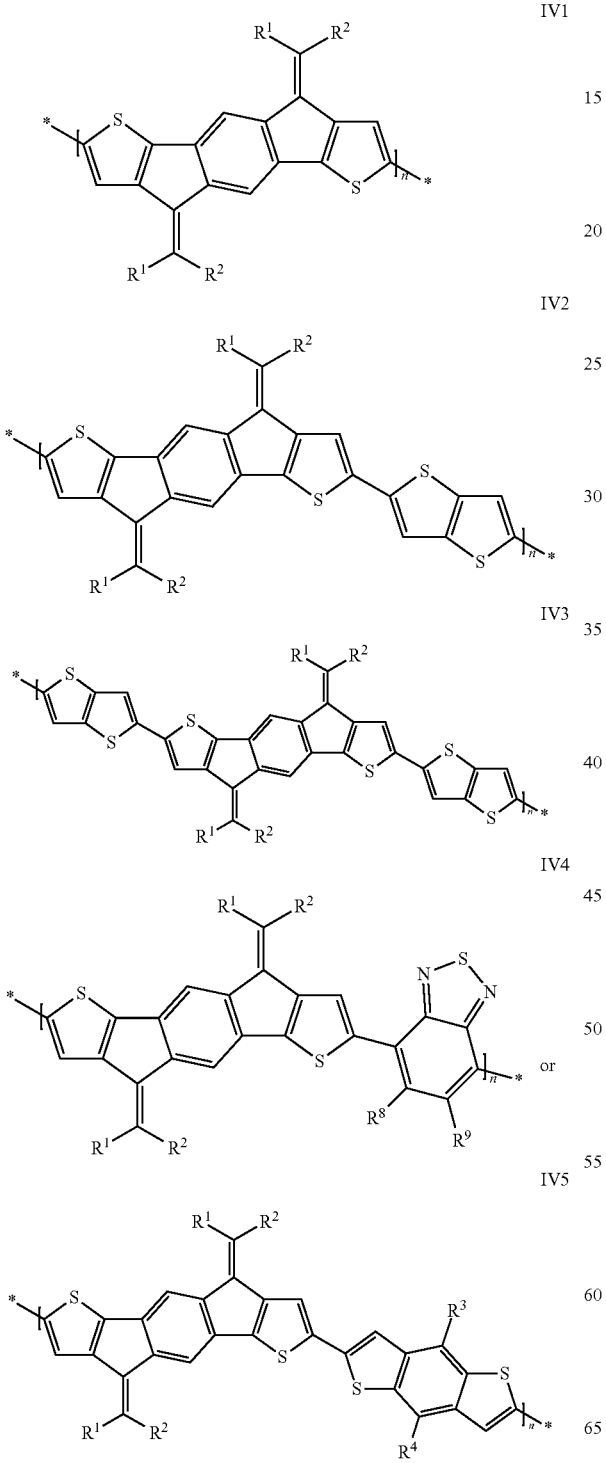

wherein R³ and R⁴ have independently of each other one of the meanings given for R¹, and * represents a linkage to an adjacent unit or group.

8. The compound according to claim 7, of formula V

wherein "chain" is a polymer chain selected of formulae IV, R⁵ and R⁶ denote, independently of each other, H, F, Br, Cl, I, —CH₂Cl, —CHO, —CRᵃ=CRᵇ₂, —SiRᵃRᵇRᶜ, —SiRᵃX'X", —SiRᵃRᵇX', —SnRᵃRᵇRᶜ, —BRᵃRᵇ, —B(ORᵃ)(ORᶜ), —B(OH)₂, —O—SO₂—Rᵃ, —C≡CH, —C≡C—SiRᵃ₃, —ZnX', —Sn(Z⁴)₃, an endcap group, or P-Sp-, wherein P is a polymerizable or crosslinkable group, Sp is a spacer group or a singlebond, X' and X" denote halogen, Rᵃ, Rᵇ and Rᶜ independently of each other denote H or alkyl with 1 to 20 C atoms, and two of Rᵃ, Rᵇ and Rᶜ may also form an aliphatic ring together with the hetero atom to which they are attached, and Z⁴ is alkyl or aryl, each being optionally substituted.

9. The compound according to claim 3, wherein one or more of Ar¹, Ar² and Ar³ denote aryl or heteroaryl of the following formulae

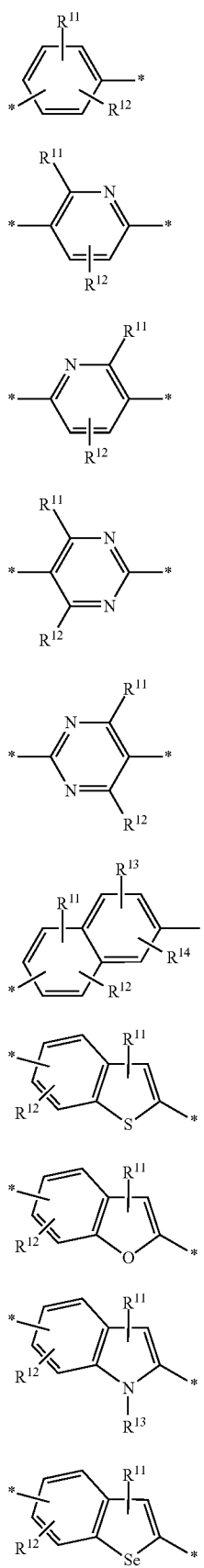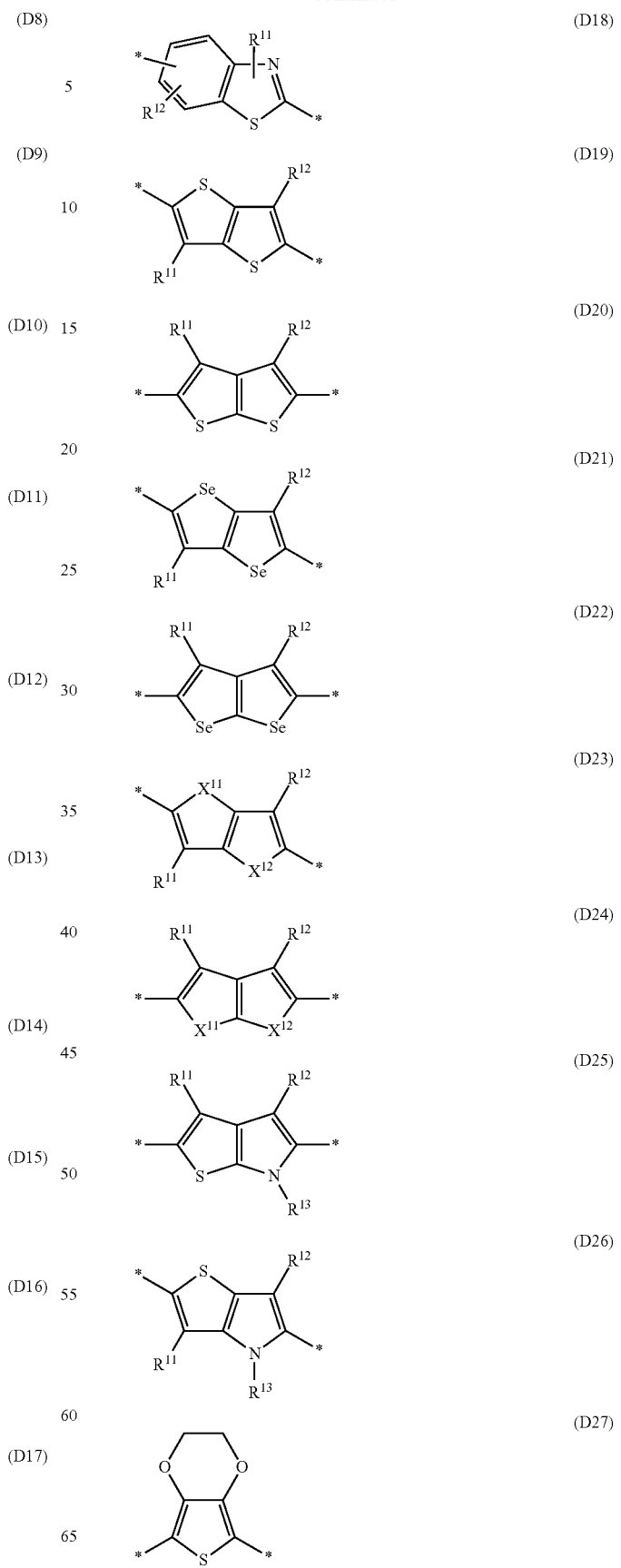

-continued
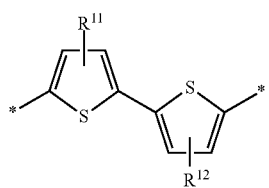 (D28)
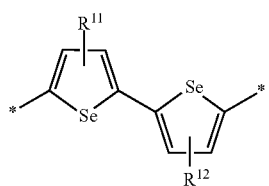 (D29)
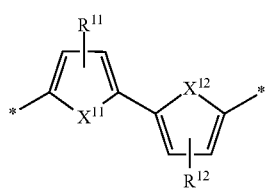 (D30)
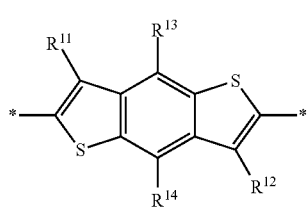 (D31)
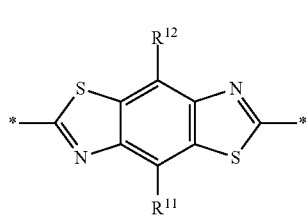 (D32)
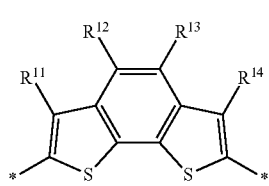 (D33)
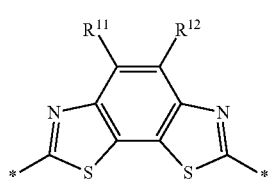 (D34)
-continued
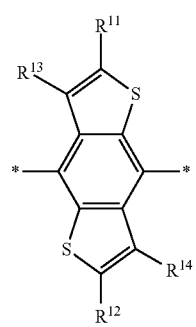 (D35)
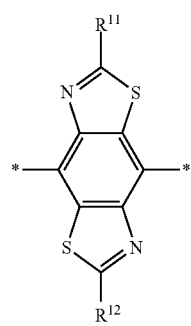 (D36)
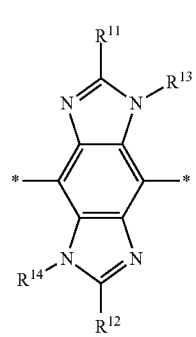 (D37)
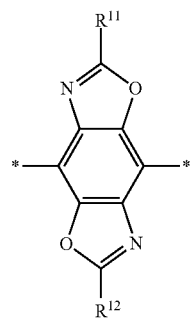 (D38)
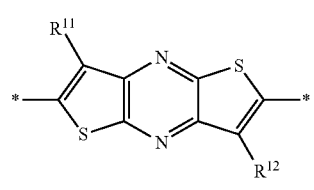 (D39)

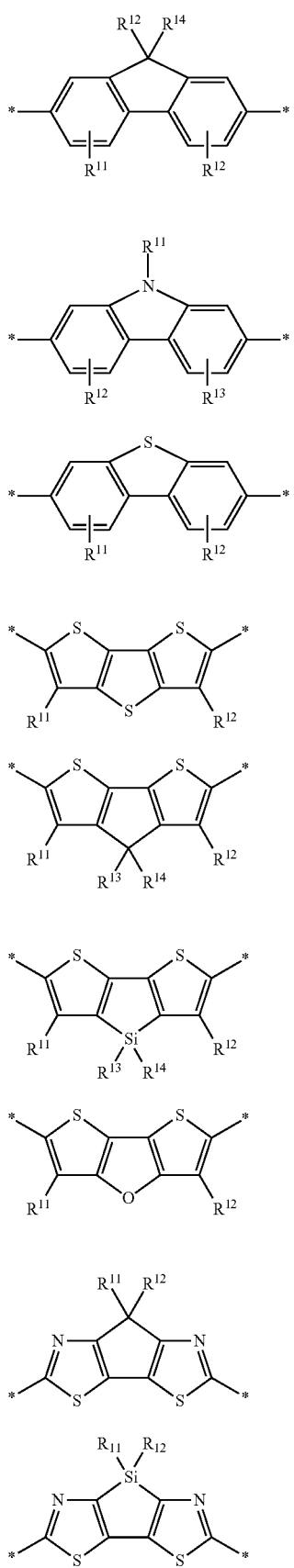

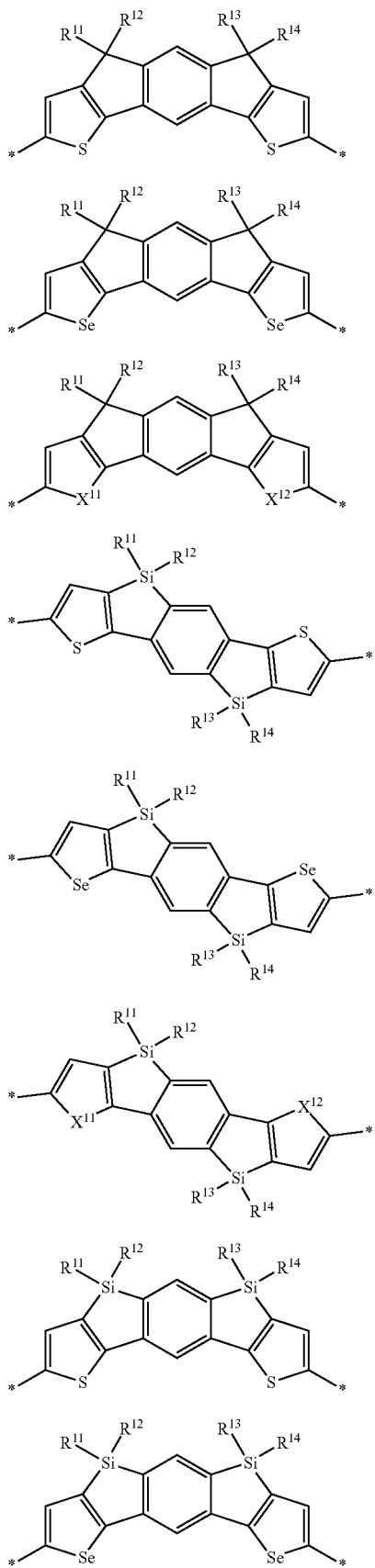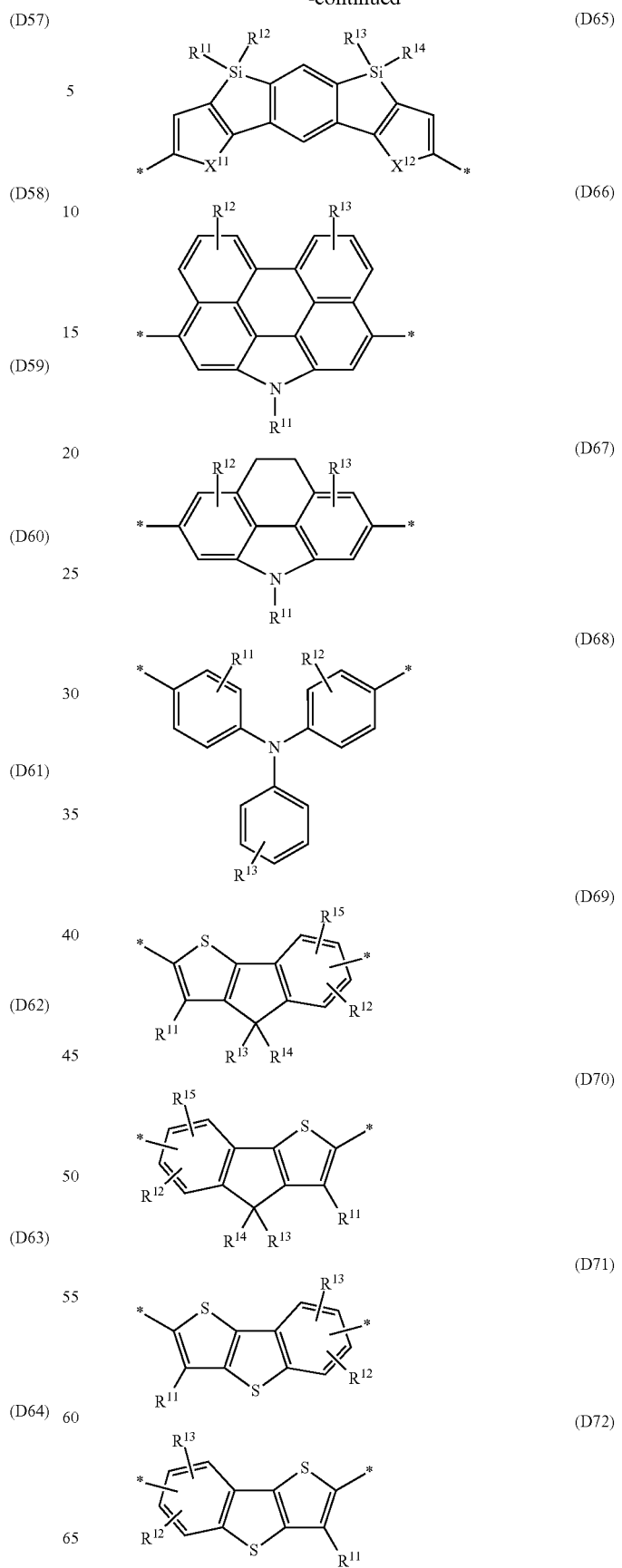

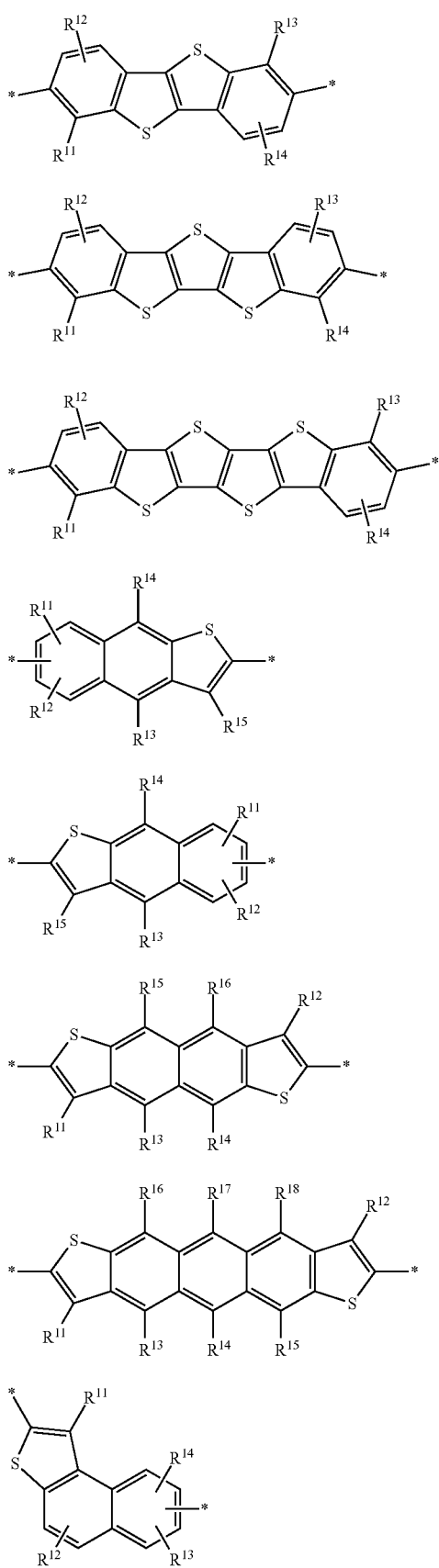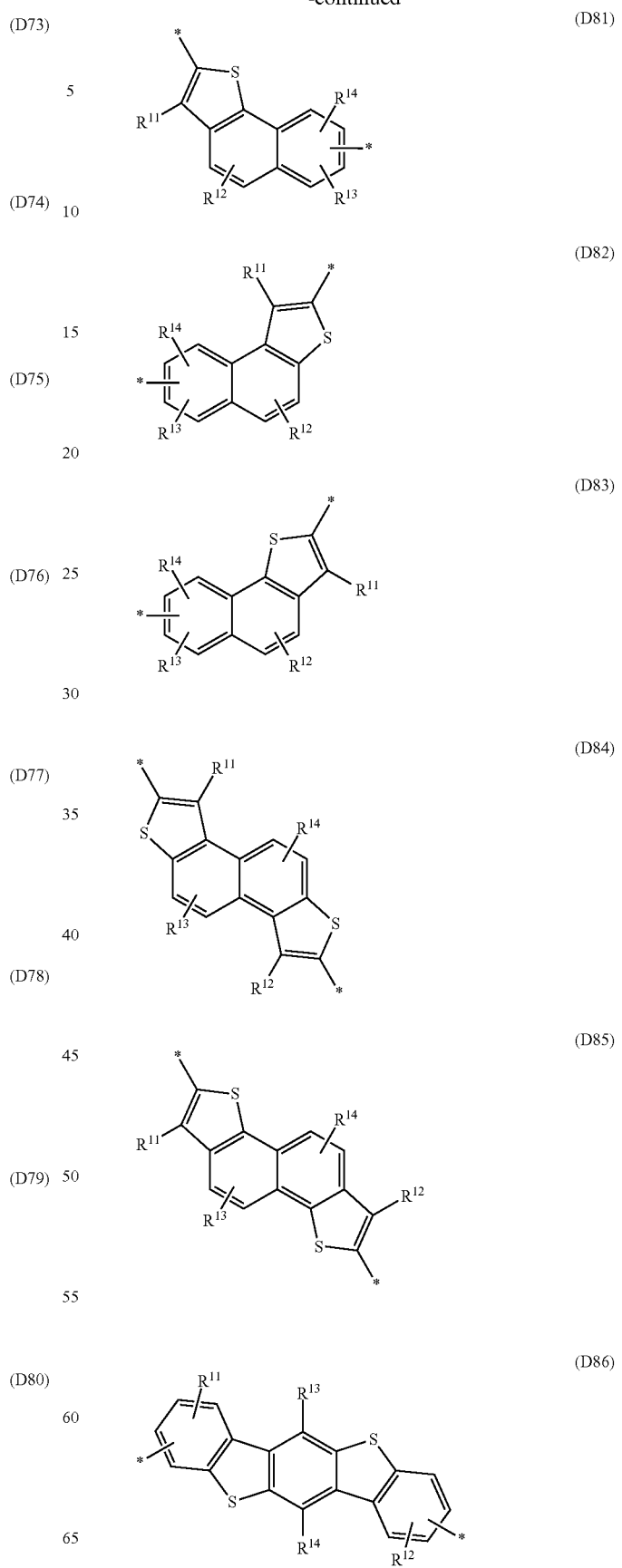

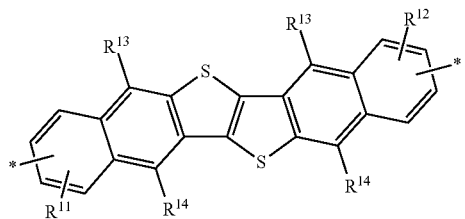
(D87)

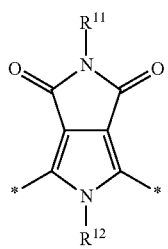
(D88)

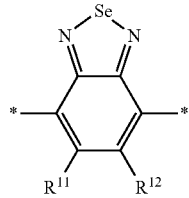
(A5)

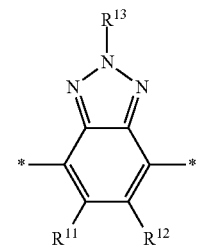
(A6)

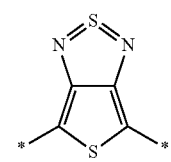
(A7)

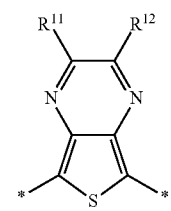
(A8)

wherein one of $X^{11}$ and $X^{12}$ is S and the other is Se, and $R^{11}$, $R^{12}$, $R^{13}$, $R^{14}$, $R^{15}$, $R^{16}$, $R^{17}$ and $R^{18}$ independently of each other denote H or have one of the meanings of $R^1$, and * represents a linkage to an adjacent unit or group.

10. The compound according to claim 4, wherein one or more of the units $Ar^3$ and $A^1$ denote aryl or heteroaryl of the following formulae

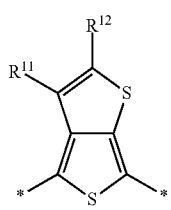
(A1)

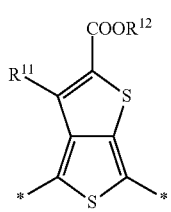
(A2)

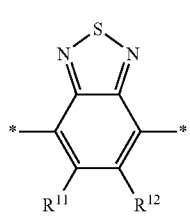
(A3)

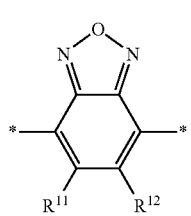
(A4)

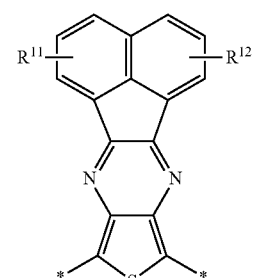
(A9)

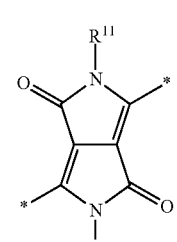
(A10)

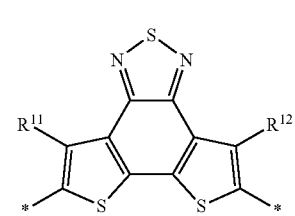
(A11)

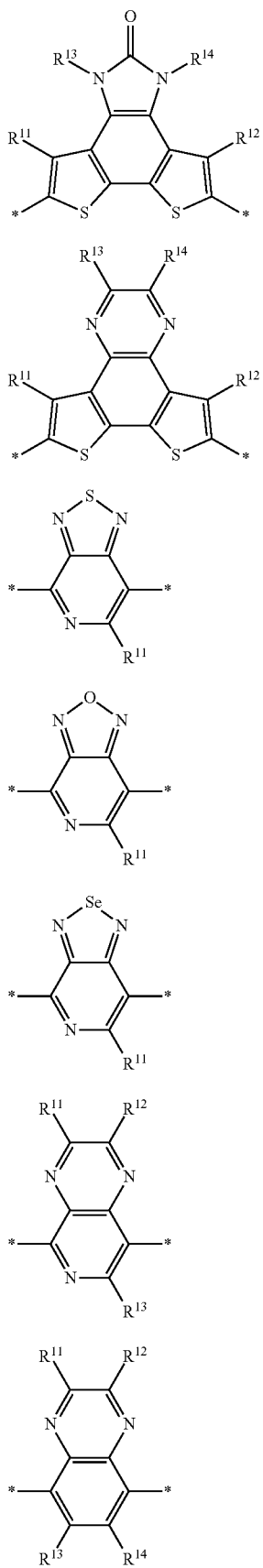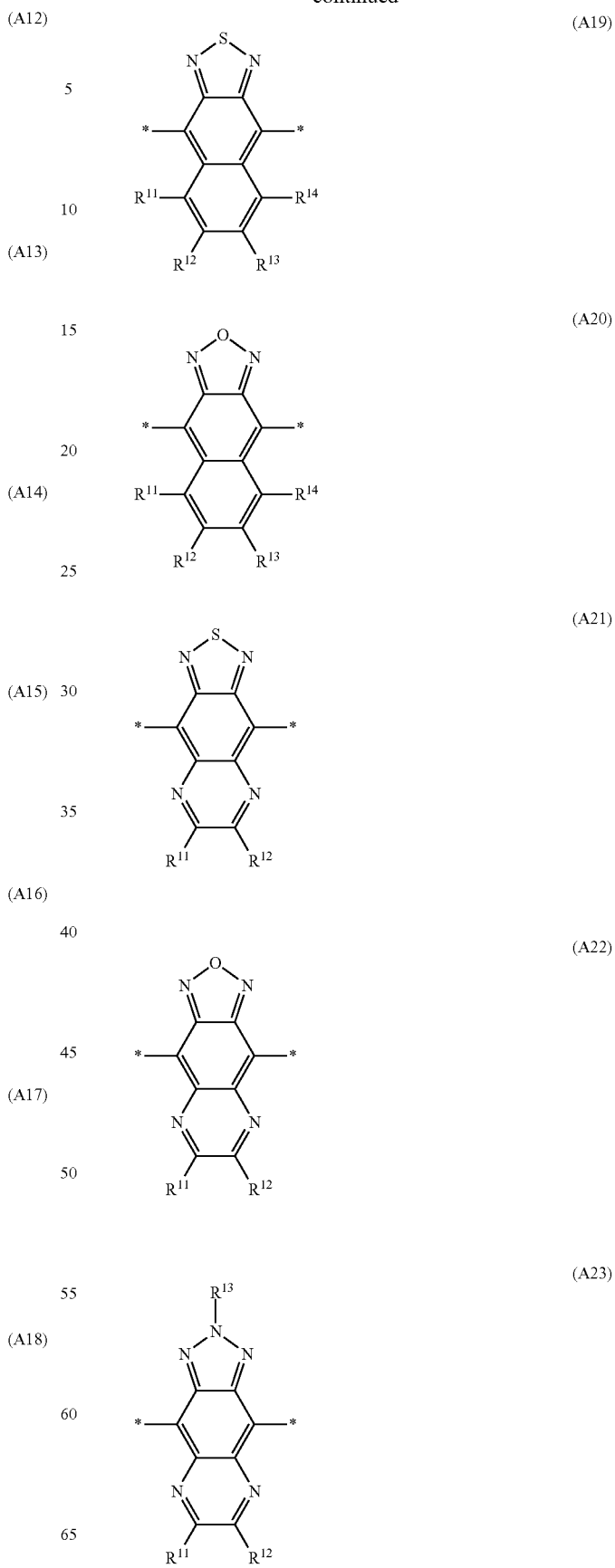

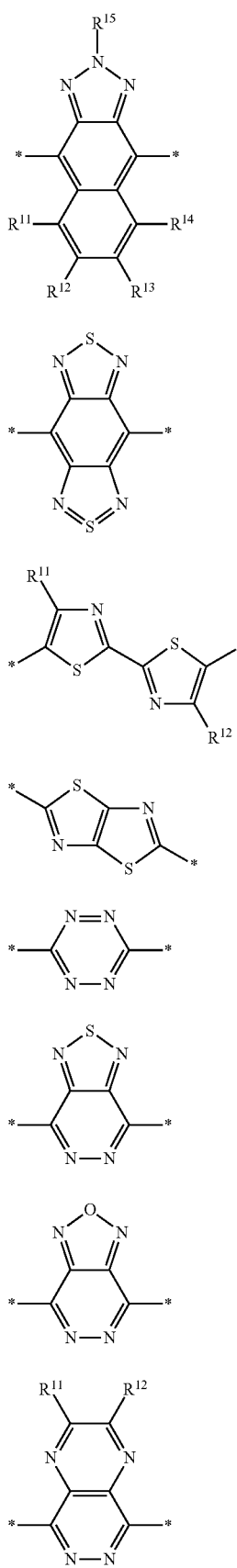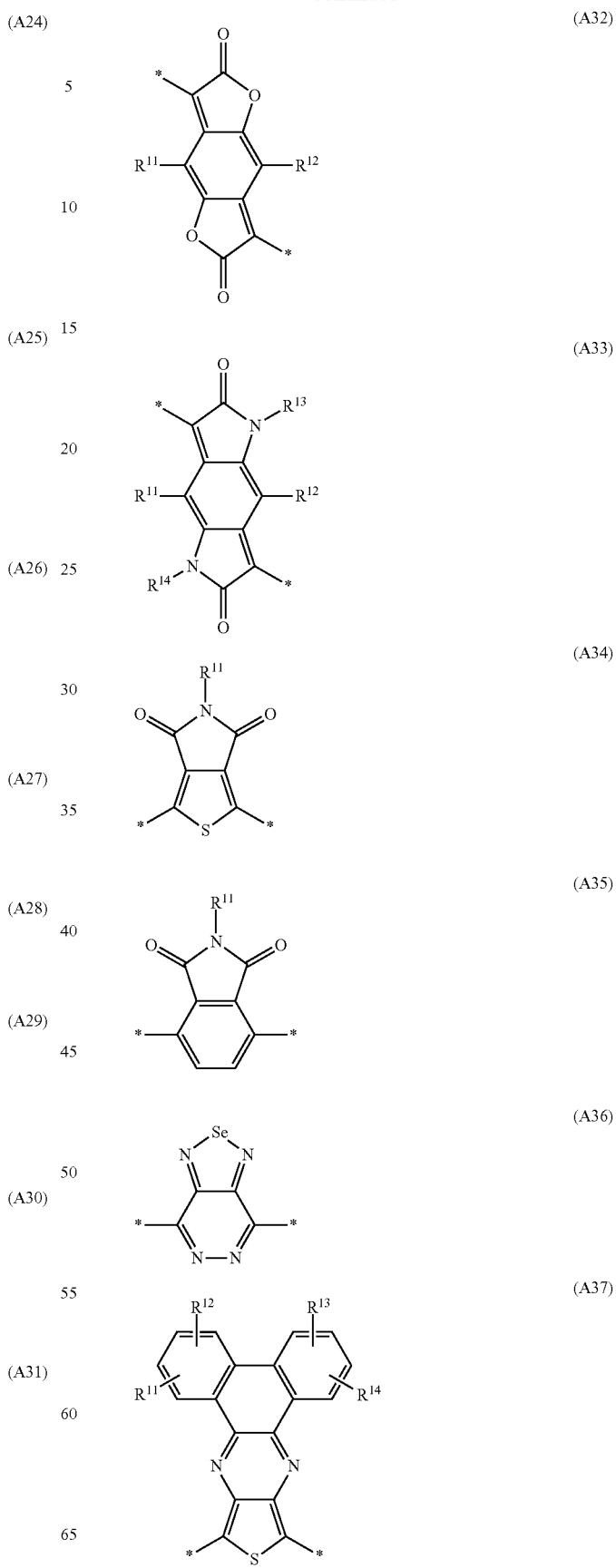

-continued

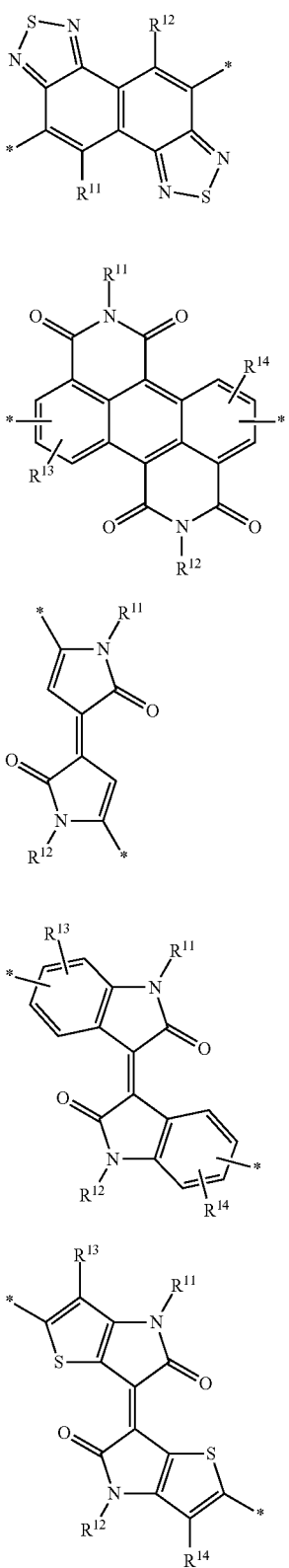

wherein one of $X^{11}$ and $X^{12}$ is S and the other is Se, and $R^{11}$, $R^{12}$, $R^{13}$, $R^{14}$ and $R^{15}$ independently of each other denote H or have one of the meanings of $R^1$, and * represents a linkage to an adjacent unit or group.

11. The compound according to claim 1, of formula VII

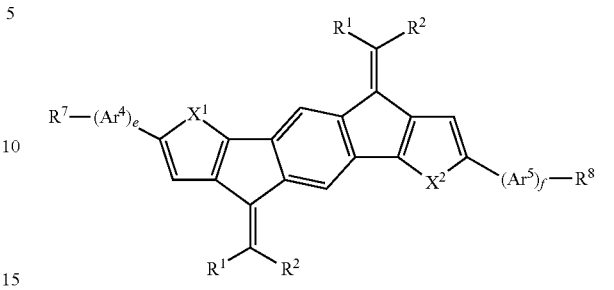

$Ar^4$, $Ar^5$ independently of each other and on each occurrence identically or differently aryl or heteroaryl that is different from U, preferably has 5 to 30 ring atoms and is optionally substituted, preferably by one or more groups $R^S$ $R^7$, $R^8$ independently of each other denote H, F, Br, Cl, —CN, —NC, —NCO, —NCS, —OCN, —SCN, —C(O)NR$^0$R$^{00}$, —C(O)X$^0$, —C(O)R$^0$, —C(O)OR$^0$, —O—C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, P-Sp-, or optionally substituted silyl, carbyl or hydrocarbyl with 1 to 40 C atoms that is optionally substituted and optionally comprises one or more hetero atoms, and wherein one or more C atoms are optionally replaced by a hetero atom, and $R^0$ and $R^{00}$ are independently of each other H or optionally substituted $C_{1-40}$ carbyl or hydrocarbyl, and $X^0$ is halogen and e and f independently of each other denote 0, 1, 2 or 3.

12. The compound according to claim 11, which is of formula VIIa

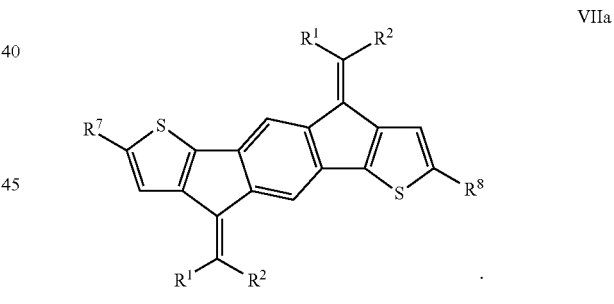

13. The compound according to claim 1, wherein $R^1$ and $R^2$ independently of each other denote straight-chain, branched or cyclic alkyl with 1 to 20 C atoms which is unsubstituted or substituted by one or more F atoms, or $R^1$ and $R^2$ independently of each other denote aryl or heteroaryl, each of which is optionally fluorinated, alkylated or alkoxylated and has 4 to 30 ring atoms, or one of $R^1$ and $R^2$ denotes H and the other is one of the aforementioned alkyl, aryl or heteroaryl groups, or $R^1$ and $R^2$ together form a cyclic alkyl group with 1 to 20 C atoms, which is unsubstituted or substituted by one or more F atoms or by one or more $C_1$-$C_{10}$ alkyl groups.

14. A mixture or blend comprising one or more compounds according to claim 1 and one or more compounds or polymers having semiconducting, charge transport, hole/electron transport, hole/electron blocking, electrically conducting, photoconducting or light emitting properties.

15. The mixture or blend according to claim 14, further comprising one or more n-type organic semiconductor compounds.

16. The mixture or blend according to claim 15, wherein the n-type organic semiconductor compound is a fullerene or substituted fullerene.

17. A formulation comprising one or more compounds, mixtures or blends according to claim 1, and one or more solvents.

18. A process of preparing a compound or monomer according to claim 11, comprising reacting an indacenodiarene of formula VIII

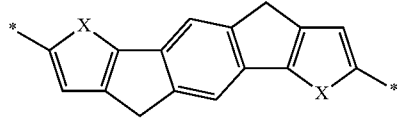

VIII wherein X is S, O, Se, Te or CH=CH, with an aldehyde or ketone of formula IX

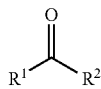

IX in a Knoevenagel condensation under alkaline conditions.

19. A charge transport, semiconducting, electrically conducting, photoconducting or light emitting material comprising a compound, mixture, blend or formulation according to claim 1.

20. An optical, electrooptical, electronic, electroluminescent or photoluminescent device, or a component thereof, or an assembly comprising it, which comprises a charge transport, semiconducting, electrically conducting, photoconducting or light emitting material, or comprises a compound, mixture, blend or formulation, according to claim 1.

21. The optical, electrooptical, electronic, electroluminescent or photoluminescent device according to claim 20, which is selected from organic field effect transistors (OFET), organic thin film transistors (OTFT), organic light emitting diodes (OLED), organic light emitting transistors (OLET), organic photovoltaic devices (OPV), organic solar cells, laser diodes, organic plasmon-emitting diodes (OPEDs), Schottky diodes, organic photoconductors (OPCs) and organic photodetectors (OPDs).

22. The device according to claim 20, which is an OFET, bulk heterojunction (BHJ) OPV device or inverted BHJ OPV device.

23. The component according to claim 20, which is selected from charge injection layers, charge transport layers, interlayers, planarising layers, antistatic films, polymer electrolyte membranes (PEM), conducting substrates and conducting patterns.

24. The assembly according to claim 20, which is integrated circuits (IC), radio frequency identification (RFID) tags or security markings or security devices containing them, flat panel displays or backlights thereof, electrophotographic devices, electrophotographic recording devices, organic memory devices, sensor devices, biosensors or biochips.

25. In batteries, or in components or devices for detecting and discriminating DNA sequences, the improvement wherein said electrode material containing electrode materials is a compound according to claim 1.

26. A monomer of formula VI

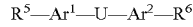

VI wherein U is a unit of formula I

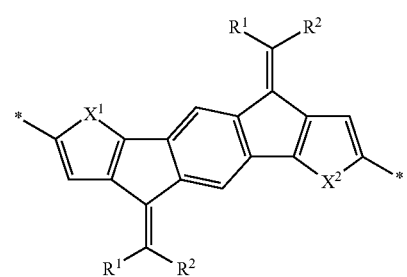

I wherein
X$^1$ and X$^2$ are independently of each other O, S, Se, Te or CH=CH,
R$^1$ and R$^2$ independently of each other, and on each occurrence identically or differently, denote H, straight-chain, branched or cyclic alkyl, with 1 to 30 C atoms, in which one or more non-adjacent C atoms are optionally replaced by —O—, —S—, —NR$^0$—, —SiR$^0$R$^{00}$—, —CY$^1$=CY$^2$— or —C≡C— in such a manner that O and/or S atoms are not linked directly to one another, and in which one or more H atoms are optionally replaced by F, Cl, Br, or I, or R$^1$ and R$^2$, independently of each other, and on each occurrence identically or differently, denote aryl, heteroaryl, aryloxy or heteroaryloxy with 4 to 20 ring atoms which is optionally substituted, or R$^1$ and R$^2$ together form an alicyclic group with 1 to 20 C atoms, which is optionally fluorinated or alkylated,
Y$^1$ and Y$^2$ are independently of each other H, F, Cl or CN,
R$^0$ and R$^{00}$ are independently of each other H or optionally substituted C$_{1-40}$ carbyl or hydrocarbyl, Ar$^1$, Ar$^2$ aryl or heteroaryl that is different from U, and is optionally substituted, optionally by one or more groups R$^S$, R$^5$ and R$^6$ are independently of each other, H, F, Br, Cl, I, —CH$_2$Cl, —CHO, —CR$^a$=CR$^b{}_2$, —SiR$^a$R$^b$R$^c$, —SiR$^a$X'X'', —SiR$^a$R$^b$X', —SnR$^a$R$^b$R$^c$, —BR$^a$R$^b$, —B(OR$^a$)(OR$^c$), —B(OH)$_2$, —O—SO$_2$—R$^a$, —C≡CH, —C≡C—SiR$^a{}_3$, —ZnX', —Sn(Z$^4$)$_3$, an endcap group, or P-Sp-, wherein P is a polymerizable or crosslinkable group, Sp is a spacer group or a singlebond, X' and X'' denote halogen, R$^a$, R$^b$ and R$^c$ independently of each other denote H or alkyl with 1 to 20 C atoms, and two of R$^a$, R$^b$ and R$^c$ may also form an aliphatic ring together with the hetero atom to which they are attached, and Z$^4$ is alkyl or aryl, each being optionally substituted, R$^S$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, and at least one of R$^5$ and R$^6$ is different from H, and * represents a linkage to an adjacent unit or group.

27. A process of preparing a polymer according to claim 2, by coupling one or more monomers of formula VI, $$R^5-Ar^1-U-Ar^2-R^6 \quad \text{VI}$$

wherein U is a unit of formula I

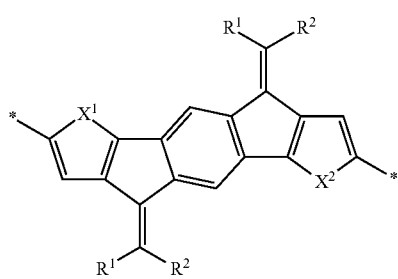

I wherein
$X^1$ and $X^2$ are independently of each other O, S, Se, Te or CH=CH,
$R^1$ and $R^2$ independently of each other, and on each occurrence identically or differently, denote H, straight-chain, branched or cyclic alkyl, with 1 to 30 C atoms, in which one or more non-adjacent C atoms are optionally replaced by —O—, —S—, —NR$^0$—, —SiR$^0$R$^{00}$—, —CY$^1$=CY$^2$— or —C≡C— in such a manner that O and/or S atoms are not linked directly to one another, and in which one or more H atoms are optionally replaced by F, Cl, Br, I or CN, or $R^1$ and $R^2$, independently of each other, and on each occurrence identically or differently, denote aryl, heteroaryl, aryloxy or heteroaryloxy with 4 to 20 ring atoms which is optionally substituted, or $R^1$ and $R^2$ together form an alicyclic group with 1 to 20 C atoms, which is optionally fluorinated or alkylated,
$Y^1$ and $Y^2$ are independently of each other H, F, Cl or CN,
$R^0$ and $R^{00}$ are independently of each other H or optionally substituted $C_{1-40}$ carbyl or hydrocarbyl, $Ar^1$, $Ar^2$ aryl or heteroaryl that is different from U, preferably has 5 to 30 ring atoms and is optionally substituted, preferably by one or more groups $R^S$, $R^5$ and $R^6$ are independently of each other, H, F, Br, Cl, I, —CH$_2$Cl, —CHO, —CR$^a$=CR$^b$$_2$, —SiR$^a$R$^b$R$^c$, —SiR$^a$X'X", —SiR$^a$R$^b$X', —SnR$^a$R$^b$R$^c$, —BR$^a$R$^b$, —B(OR$^a$)(OR$^c$), —B(OH)$_2$, —O—SO$_2$—R$^a$, —C≡CH, —C≡C—SiR$^a$$_3$, —ZnX', —Sn(Z$^4$)$_3$, an endcap group, or P-Sp-, wherein P is a polymerizable or crosslinkable group, Sp is a spacer group or a singlebond, X' and X" denote halogen, $R^a$, $R^b$ and $R^c$ independently of each other denote H or alkyl with 1 to 20 C atoms, and two of $R^a$, $R^b$ and $R^c$ may also form an aliphatic ring together with the hetero atom to which they are attached, and $Z^4$ is alkyl or aryl, each being optionally substituted, and at least one of $R^5$ and $R^6$ is different from H, wherein $R^5$ and $R^6$ are halogen, stannyl or boronate groups, with each other and/or with one or more monomers of the following formulae $$R^5-Ar^3-R^6 \quad \text{C1}$$

$$R^5-A^1-R^6 \quad \text{C2}$$

wherein $Ar^3$ is aryl or heteroaryl that is different from U, and is optionally substituted, optionally by one or more groups $R^S$, $A^1$ is an aryl or heteroaryl group that is different from U and $Ar^{1-3}$, has 5 to 30 ring atoms, is optionally substituted by one or more groups $R^S$ and is selected from aryl or heteroaryl groups having electron donor properties, $R^S$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, $R^5$ and $R^6$ are halogen, stannyl or boronate groups, in an aryl-aryl coupling reaction.

28. The process according to claim 18, further comprising adding halogen, trialkylstannyl or boronate groups in 2- and 7-position of the product of the process of claim 18 by i) halogenation with N-halosuccinimide or elemental halogen, or ii) lithiation with alkyllithium and lithium amide, followed by reaction with a halogenation reagent, an alkyl borate, a trialkylstannyl chloride or zinc chloride.

* * * * *